(12) United States Patent
Layton et al.

(10) Patent No.: US 12,305,185 B2
(45) Date of Patent: May 20, 2025

(54) EXPRESSION VECTOR AND METHOD

(71) Applicant: MOUNT SPEC INVESTMENTS PTY LTD, Queensland (AU)

(72) Inventors: Christopher Layton, Queensland (AU); Jason Steel, Queensland (AU)

(73) Assignee: MOUNT SPEC INVESTMENTS PTY LTD, Queensland (AU)

( * ) Notice: Subject to any disclaimer, the term of this patent is extended or adjusted under 35 U.S.C. 154(b) by 1197 days.

(21) Appl. No.: 16/963,880

(22) PCT Filed: Jan. 23, 2019

(86) PCT No.: PCT/AU2019/050046
§ 371 (c)(1),
(2) Date: Jul. 22, 2020

(87) PCT Pub. No.: WO2019/144186
PCT Pub. Date: Aug. 1, 2019

(65) Prior Publication Data
US 2021/0207166 A1 Jul. 8, 2021

(30) Foreign Application Priority Data

Jan. 23, 2018 (AU) ................ 2018900206

(51) Int. Cl.
C12N 15/86 (2006.01)
A61K 9/00 (2006.01)
A61K 31/192 (2006.01)
A61K 31/65 (2006.01)
A61P 27/02 (2006.01)
A61P 37/06 (2006.01)
C12N 7/00 (2006.01)
A61K 48/00 (2006.01)

(52) U.S. Cl.
CPC ............ *C12N 15/86* (2013.01); *A61K 9/0048* (2013.01); *A61K 31/192* (2013.01); *A61K 31/65* (2013.01); *A61P 27/02* (2018.01); *A61P 37/06* (2018.01); *C12N 7/00* (2013.01); *A61K 48/00* (2013.01); *C12N 2750/14143* (2013.01); *C12N 2800/30* (2013.01); *C12N 2830/003* (2013.01); *C12N 2830/006* (2013.01); *C12N 2830/20* (2013.01)

(58) Field of Classification Search
CPC ............ C12N 15/86; C12N 2830/003; C12N 2830/006; C12N 2830/002; C12N 2830/005
See application file for complete search history.

(56) References Cited

FOREIGN PATENT DOCUMENTS

| CN | 103352053 | 10/2013 |
|----|-----------|---------|
| WO | 00/07601 | 2/2000 |
| WO | 01/58494 | 8/2001 |
| WO | 01/59088 | 8/2001 |
| WO | 02/088346 | 11/2002 |
| WO | 2013/049493 | 4/2013 |
| WO | 2013/159103 | 10/2013 |
| WO | 2016/205825 | 12/2016 |
| WO | 2017/106244 | 6/2017 |

OTHER PUBLICATIONS

Perez 2002, Human Gene Therapy 13:2161-2172.*
Apparailly 2002, Human Gene Therapy 13:1179-1188.*
Maltzman JS, Turka LA. Conditional gene expression: a new tool for the transplantologist. Am J Transplant. 2007;7(4):733-740. doi:10.1111/j.1600-6143.2006.01685.x.
Hsiao, Edward C., et al. "Constitutive Gs activation using a single-construct tetracycline-inducible expression system in embryonic stem cells and mice." Stem cell research & therapy 2.2 (2011): 1-12.
Gomez-Gutierrez, Jorge G., et al. "Developing adenoviral vectors encoding therapeutic genes toxic to host cells: comparing binary and single-inducible vectors expressing truncated E2F-1." Virology 397.2 (2010): 337-345.
Park, Jae Yoon et al. "Dual regulation of gene expression mediated by tetracycline and Cre recombinase." BioTechniques vol. 36,3 (2004): 390-2, 394, 396. doi:10.2144/04363BM03.
Giry-Laterrière, Marc, Els Verhoeyen, and Patrick Salmon. "Lentiviral vectors." Viral vectors for gene therapy: methods and protocols (2011): 183-209.

* cited by examiner

*Primary Examiner* — Valarie E Bertoglio
(74) *Attorney, Agent, or Firm* — Robin L. Teskin; Baker, Donelson, Bearman, Caldwell & Berkowitz PC

(57) ABSTRACT

The present disclosure relates to regulatable expression vectors for systematically controlling and silencing expression of a therapeutic molecule and uses thereof, e.g. treating ocular disorders such as choroidal neovascularisation.

Figure 1:
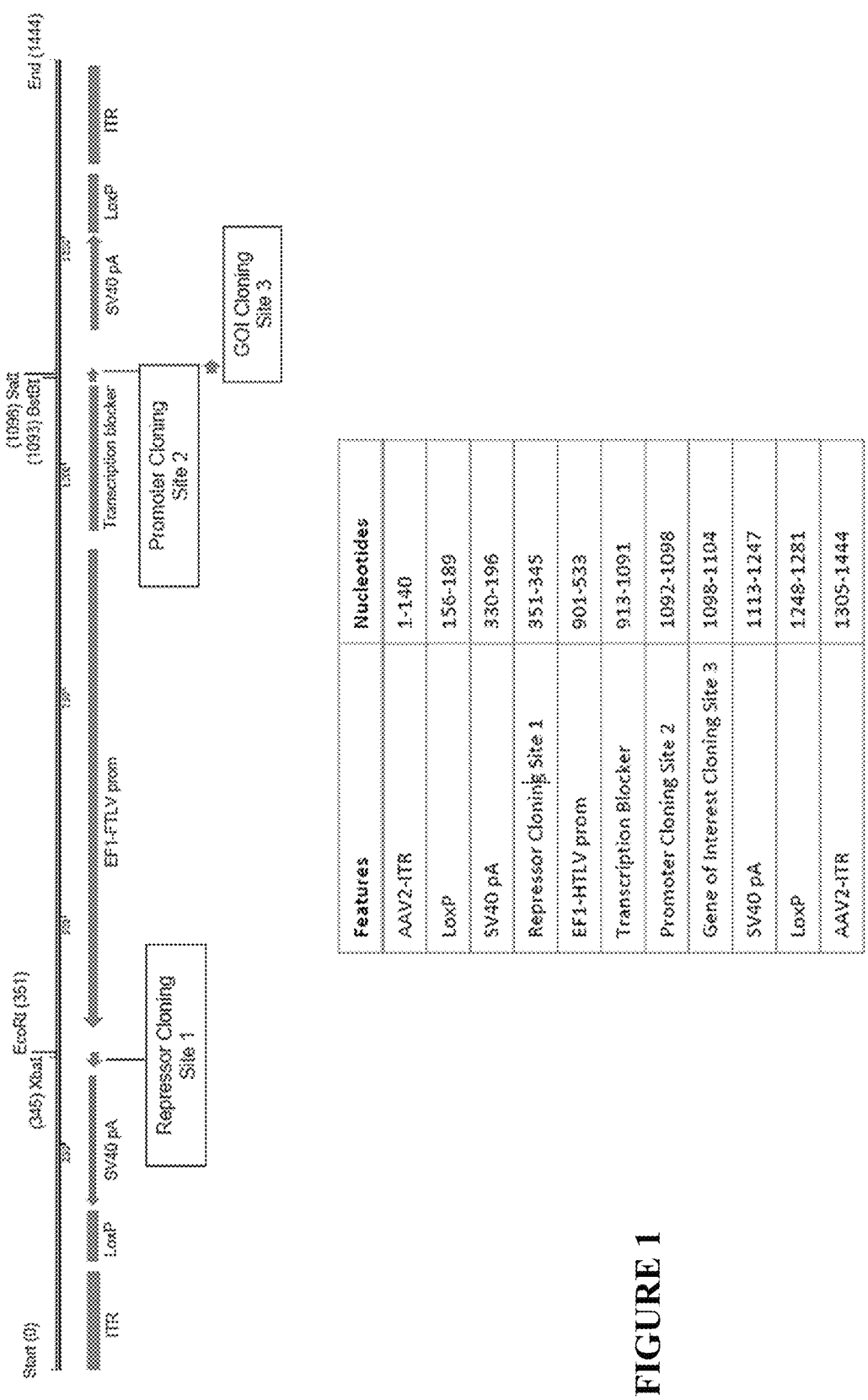

10 Claims, 13 Drawing Sheets
Specification includes a Sequence Listing.

SEQUENCE LISTING

```
<160> NUMBER OF SEQ ID NOS: 48

<210> SEQ ID NO 1
<211> LENGTH: 1444
<212> TYPE: DNA
<213> ORGANISM: Artificial Sequence
<220> FEATURE:
<223> OTHER INFORMATION: Synthetic

<400> SEQUENCE: 1
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc tgcggccgca cgcgtataac ttcgtatagc atacattata     180
cgaagttata gatctaactt gtttattgca gcttataatg gttacaaata aggcaatagc     240
atcacaaatt tcacaaataa ggcatttttt tcactgcatt ctagttttgg tttgtccaaa     300
ctcatcaatg tatcttatca tgtctggatc tactcgagct gcagtctaga gaattcacct     360
gcaggccagt aggcgccggt cacagcttgg atctgtaacg gcgcagaaca gaaaacgaaa     420
caaagacgta gagttgagca agcagggtca ggcaaagcgt ggagagccgg ctgagtctag     480
gtaggctcca agggagcgcc ggacaaaggc ccggtctcga cctgagcttt aaacttacct     540
agacggcgga cgcagttcag gaggcaccac aggcgggagg cggcagaacg cgactcaacc     600
ggcgtggatg gcggcctcag gtagggcggc gggcgcgtga aggagagatg cgagcccctc     660
gaagcttcag ctgtgttctg gcggcaaacc cgttgcgaaa aagaacgttc acggcgacta     720
ctgcacttat atacggttct cccccaccct cgggaaaaag gcggagccag tacacgacat     780
```

| | |
|---|---:|
| cactttccca gtttacccog cgccaccttc tctaggcacc cgttcaattg ccgaccccte | 840 |
| cccccaactt ctcggggact gtgggcgatg tgcgctctgc ccactgacgg gcaccggagc | 900 |
| gatcgcagat ccgtggaatt atcacctcga gaataaaata tctttatttt cattacatct | 960 |
| gtgtgttggt ttttgtgtg aatcgatagt actaacatac gctctccatc aaaacaaaac | 1020 |
| gaaacaaaac aaactagcaa aataggctgt ccccagtgca agtgcaggtg ccagaacatt | 1080 |
| tctctctcga gttcgaagtc gacgctagct gggatccaga catgataaga tacattgatg | 1140 |
| agtttggaca aaccaaaact agaatgcagt gaaaaaaatg ccttatttgt gaaatttgtg | 1200 |
| atgctattgc cttatttgta accattataa gctgcaataa acaagttata acttcgtata | 1260 |
| gcatacatta tacgaagtta tcacgtgcgg accgagcggc cgcaggaacc cctagtgatg | 1320 |
| gagttggcca ctccctctct gcgcgctcgc tcgctcactg aggccgggcg accaaaggtc | 1380 |
| gcccgacgcc cgggctttgc ccgggcggcc tcagtgagcg agcgagcgcg cagctgcctg | 1440 |
| cagg | 1444 |

<210> SEQ ID NO 2
<211> LENGTH: 747
<212> TYPE: DNA
<213> ORGANISM: Artificial Sequence
<220> FEATURE:
<223> OTHER INFORMATION: Synthetic

<400> SEQUENCE: 2

| | |
|---|---:|
| atgtctagac tggacaagag caaagtcata aacggagctc tggaattact caatggtgtc | 60 |
| ggtatcgaag gcctgacgac aaggaaactc gctcaaaagc tgggagttga gcagcctacc | 120 |
| ctgtactggc acgtgaagaa caagcgggcc ctgctcgatg ccctgccaat cgagatgctg | 180 |
| gacaggcatc atacccactt ctgccccctg gaaggcgagt catggcaaga ctttctgcgg | 240 |
| aacaacgcca agtcataccg ctgtgctctc ctctcacatc gcgacggggc taaagtgcat | 300 |
| ctcggcaccc gcccaacaga gaaacagtac gaaaccctgg aaaatcagct cgcgttcctg | 360 |
| tgtcagcaag gcttctccct ggagaacgca ctgtacgctc tgtccgccgt gggccacttt | 420 |
| acactgggct gcgtattgga ggaacaggag catcaagtag caaaagagga agagagaca | 480 |
| cctaccaccg attctatgcc cccacttctg agacaagcaa ttgagctgtt cgaccggcag | 540 |
| ggagccgaac ctgccttcct tttcggcctg gaactaatca tatgtggcct ggagaaacag | 600 |
| ctaaagtgcg aaagcggcgg gccgaccgac gcccttgacg attttgactt agacatgctc | 660 |
| ccagccgatg cccttgacga ctttgacctt gatatgctgc ctgctgacgc tcttgacgat | 720 |
| tttgaccttg acatgctccc cgggtaa | 747 |

<210> SEQ ID NO 3
<211> LENGTH: 617
<212> TYPE: DNA
<213> ORGANISM: Artificial Sequence
<220> FEATURE:
<223> OTHER INFORMATION: Synthetic

<400> SEQUENCE: 3

| | |
|---|---:|
| atgagtccaa agagaagaac acaggcagag cgcgcaatgg agacccaggg caagttgatt | 60 |
| gcagcggccc tgggggtttt acgggaaaaa ggttacgcgg gattccggat cgcagatgtg | 120 |
| cccggtgctg caggtgtctc gagaggagcg cagagccatc atttcccgac aaagcttgag | 180 |
| cttctgcttg ccacttttga atggctttac gaacagatca ccgaacgcag tcgggctcga | 240 |
| ttagcgaaat tgaagccaga ggatgacgtc atccagcaaa tgctggacga cgccgccgaa | 300 |

```
tttttcctcg acgatgactt ctctatcagc cttgatttga ttgtggctgc cgaccgggat    360
ccagcgttac gcgagggtat tcagcgcacg gtagagagga atcggtttgt cgtcgaggat    420
atgtggcttg gtgttctggt gagccgtggt cttcgcgtg atgatgcaga agatatcctt    480
tggttgatat tcaattcggt gcgtgggctt gctgttcgta gcctatggca gaaggacaaa    540
gaacgctttg agcgtgtcag gaactcgaca ctcgaaattg cgcgagagcg gtacgcgaaa    600
ttcaagcgct agtctag                                                   617

<210> SEQ ID NO 4
<211> LENGTH: 315
<212> TYPE: DNA
<213> ORGANISM: Artificial Sequence
<220> FEATURE:
<223> OTHER INFORMATION: Synthetic

<400> SEQUENCE: 4
gagtttactc cctatcagtg atagagaacg tatgtcgagt ttactcccta tcagtgatag     60
agaacgatgt cgagtttact ccctatcagt gatagagaac gtatgtcgag tttactccct    120
atcagtgata gagaacgtat gtcgagttta ctccctatca gtgatagaga acgtatgtcg    180
agtttatccc tatcagtgat agagaacgta tgtcgagttt actccctatc agtgatagag    240
aacgtatgtc gaggtaggcg tgtacggtgg gaggcctata aagcagagc tcgtttagtg     300 aaccgtcaga tcgcc                                                     315

<210> SEQ ID NO 5
<211> LENGTH: 584
<212> TYPE: DNA
<213> ORGANISM: Artificial Sequence
<220> FEATURE:
<223> OTHER INFORMATION: Synthetic

<400> SEQUENCE: 5
cctaggcgtt acataactta cggtaaatgg cccgcctggc tgaccgccca acgaccccg      60 cccattgacg tcaataatga cgtatgttcc catagtaacg ccaataggga ctttccattg    120
acgtcaatgg gtggagtatt tacggtaaac tgcccacttg gcagtacatc aagtgtatca    180
tatgccaagt ccgccccta ttgacgtcaa tgacggtaaa tggcccgcct ggcattatgc     240
ccagtacatg accttacggg actttcctac ttggcagtac atctacgtat tagtcatcgc    300
tattaccatg gtgatgcggt tttggcagta caccaatggg cgtggatagc ggtttgactc    360
acggggattt ccaagtctcc accccattga cgtcaatggg agtttgtttt ggcaccaaaa    420
tcaacgggac tttccaaaat gtcgtaataa ccccgccccg ttgacgcaaa tgggcaagct    480
tgccgggtcg aggtaggcgt gtacggtggg aggcctatat aagcaaccgg tataatacaa    540
acagaccaga ttgtctgttt gttcaattgg aagaaggatc ctct                     584

<210> SEQ ID NO 6
<211> LENGTH: 621
<212> TYPE: DNA
<213> ORGANISM: Artificial Sequence
<220> FEATURE:
<223> OTHER INFORMATION: Synthetic

<400> SEQUENCE: 6
gggtcattag ttcatagccc atatatggag ttccgcgtta cataacttac ggtaaatggc     60
ccgcctggct gaccgcccaa cgaccccgc ccattgacgt caataatgac gtatgttccc     120
```

```
atagtaacgt caatagggac tttccattga cgtcaatggg tggagtattt acggtaaact    180
gcccacttgg cagtacatca agtgtatcat atgccaagta cgccccctat tgacgtcaat    240
gacggtaaat ggcccgcctg gcattatgcc cagtacatga ccttatggga ctttcctact    300
tggcagtaca tctacgtatt agtcatcgct attaccatgg tgatgcggtt ttggcagtac    360
atcaatgggc gtggatagcg gtttgactca cggggatttc caagtctcca ccccattgac    420
gtcaatggga gtttgttttg caccaaaatc aacgggactt tccaaaatgt cgtaacaact    480
ccgccccatt gacgcaaatg ggcggtaggc gtgtacggtg ggaggtctat ataagcagag    540
ctcgtttagt gaaccgtcag atcgcctgga gacgccatcc acgctgtttt gacctccata    600
gaagacaccg ggaccgatcc a                                              621

<210> SEQ ID NO 7
<211> LENGTH: 726
<212> TYPE: DNA
<213> ORGANISM: Artificial Sequence
<220> FEATURE:
<223> OTHER INFORMATION: Synthetic

<400> SEQUENCE: 7
atggtttcta aggagaaga actctttact ggtgttgtcc caattctggt tgagctggat     60
ggtgatgtga atggccacaa attctctgtg tctggtgaag gtgaaggaga tgcaacttat    120
ggaaagctga ctctgaagtt catttgtaca acaggaaagc tgccagtgcc ttggccaact    180
ctggtgacca ccctgactta tggtgttcaa tgtttcagca ggtaccctga ccacatgaag    240
cagcatgact ctctttaaatc tgcaatgcca gaaggttatg ttcaggagag acaatcttc    300
tttaaggatg atggaaatta taagacaagg gcagaagtga agtttgaagg tgatacactg    360
gttaacagaa ttgagctgaa aggcattgat tttaaggaag atggaaacat tctgggtcac    420
aagctggagt acaactataa ttctcacaat gtttacatta tggcagataa gcagaggaat    480
ggaattaagg ctaatttcaa gattagacac aacattgagg atggatctgt ccaactggca    540
gaccattacc agcagaacac ccctattggt gatggcccag ttctcctccc agataatcac    600
tatctcagca ctcaatctgc tctgtccaaa gaccctaatg agaaaagaga ccacatggtc    660
ctcctggagt ttgtgacagc agcaggaatt actctgggaa tggatgagct gtacaagtaa    720
agctag                                                              726

<210> SEQ ID NO 8
<211> LENGTH: 570
<212> TYPE: DNA
<213> ORGANISM: Homo sapiens

<400> SEQUENCE: 8
atgcacagct cagcactgct ctgttgcctg gtcctcctga ctggggtgag ggccagccca     60
ggccagggca cccagtctga aacagctgc acccacttcc caggcaacct gcctaacatg    120
cttcgagatc tccgagatgc cttcagcaga gtgaagactt tctttcaaat gaaggatcag    180
ctggacaact tgttgttaaa ggagtccttg ctggaggact taagggtta cctgggttgc    240
caagccttgt ctgagatgat ccagttttac tggaggagg tgatgcccca agctgagaac    300
caagacccag acatcaaggc gcatgtgaac tcctggggg agaacctgaa gaccctcagg    360
ctgaggctac ggcgctgtca tcgatttctt ccctgtgaaa acaagagcaa ggccgtggag    420
caggtgaaga atgcctttaa taagctccaa gagaaaggca tctacaaagc catgagtgag    480
tttgacatct tcatcaacta catagaagcc tacatgacaa tgaagataag aaactgagac    540
```

```
atcagggtgg cgactctata gactcgctag                                        570
```

<210> SEQ ID NO 9
<211> LENGTH: 1739
<212> TYPE: DNA
<213> ORGANISM: Artificial Sequence
<220> FEATURE:
<223> OTHER INFORMATION: Synthetic

<400> SEQUENCE: 9

```
atgtacagaa tgcagctgct gagctgtatc gccctgtctc tggccctggt cacaaactct        60
gcccacagcc acagagactt ccagcctgtg ctgcatctgg tggccctgaa ctctccactg       120
tctggcggca tgagaggcat cagaggcgcc gacttccagt gtttccagca ggctagagct       180
gtcggcctgg ccggaacatt cagagccttt ctgagcagca gactgcagga cctgtacagc       240
atcgtgcgga gagccgatag agccgctgtg cctatcgtga acctgaagga cgagctgctg       300
ttccctagct gggaagctct gttctctggc agcgagggac tctgaaaccc aggcgccaga       360
atcttcagct tcgacggcaa ggacgtgctg agacacccta cctggcctca gaaatctgtg       420
tggcacggca gcgatcccaa cggcagaagg ctgacagaga gctactgcga gacttggagg       480
acagaggccc ctagcgctac aggccaagca agctcacttc tcggaggcag actgctggga       540
cagtctgccg cttcttgtca ccacgcctac atcgtgctgt gcatcgagaa cagcttcatg       600
accgccagca aggtgccagg cgtgggaaca atagcgtgt acctgagcga gtgcaagacc        660
ggcaacggca agaactacag aggcaccatg agcaagacca gaacggcat cacctgtcag        720
aagtggtcca gcacaagccc tcacagaccc agattcagcc ctgctacaca cccaagcgaa       780
ggcctggaag agaactactg cagaaacccc gacaacgacc tcaaggccc ttggtgctac        840
accaccgatc ctgagaagag atacgactac tgcgacatcc tggaatgcga agaggaatgc       900
atgcactgca gcggcgagaa ctacgatggc aagatctcca agaccatgag cggcctcgag       960
tgtcaggcct gggattctca gtctcctcac gctcacggct acatcccag caagttcccc       1020
aacaagaatc tgaagaagaa ttactgtcgg aaccccgacc gcgagctgag gccttggtgt      1080
ttcacaacag accctaacaa gagatgggag ctgtgtgaca tccctagatg caccacacct      1140
ccaccttcta gcggccctac ctaccagtgt ctgaaaggca ccggcgagaa ttacaggggc      1200
aatgtggccg tgaccgtgtc tggacacaca tgccaacatt ggagcgccca gacacctcac      1260
acacacaaca gaacccctga gaacttcccc tgcaagaacc tggacgaaaa ctattgccgg      1320
aatcctgacg gcaagagggc cccttggtgt cacactacca cagccaagt ccgctgggag       1380
tactgcaaga tccccagctg tgacagcagc cctgtgtcta cagaacagct ggccctaca       1440
gctcctcctg agctgacacc tgtggtgcag gactgttatc acggcgacgg ccagtcctac      1500
agaggaacaa gcagcaccac cacaaccggc aagaagtgcc agagctggtc tagcatgacc      1560
cctcacaggc accagaaaac cccagagaat taccccaacg ccggcctgac catgaactac      1620
tgtaggaatc cagacgccga caaggcccc tggtgtttta ccacagatcc cagcgtcaga       1680
tgggaatact gtaacctgaa gaagtgcagc ggcaccgagg ccagcgttgt gtgagctag        1739
```

<210> SEQ ID NO 10
<211> LENGTH: 542
<212> TYPE: DNA
<213> ORGANISM: Homo sapiens

<400> SEQUENCE: 10

| | |
|---|---:|
| atggaaatct gcaggggacc ttacagtcac ctaatctctc tccttctcat ccttctgttt | 60 |
| cgttcagagt cagctggcca ccctgctggg aaaagaccct gcaagatgca agccttcaga | 120 |
| atctgggata ctaaccagaa gaccttctac ctgaggaaca accagctcat tgctgggtac | 180 |
| ttacaaggac caaataccaa actagaagaa aagatagaca tggtgcctat tgactttcgg | 240 |
| aatgtgttct tgggcatcca cggggggcaag ctgtgcctgt cttgtgtcaa gtctggagat | 300 |
| gacaccaagc tccagctgga ggaggttaac atcactgatc tgaacaagaa caaagaagaa | 360 |
| gacaagcgct ttaccttcat ccgctccgag acaggcccta ccaccagctt cgaatcactt | 420 |
| gcctgtccag gatggttcct ctgcacaaca ctagaggctg atcatcccgt gagcctcacc | 480 |
| aacacaccaa aagagccctg tacagtcaca aagttctact tccaggaaga ccaataggct | 540 |
| ag | 542 |

<210> SEQ ID NO 11
<211> LENGTH: 2315
<212> TYPE: DNA
<213> ORGANISM: Artificial Sequence
<220> FEATURE:
<223> OTHER INFORMATION: Synthetic

<400> SEQUENCE: 11

| | |
|---|---:|
| atgcacagct cagcactgct ctgttgcctg gtcctcctga ctggggtgag ggccagccca | 60 |
| ggccagggca cccagtctga aacagctgc acccacttcc caggcaacct gcctaacatg | 120 |
| cttcgagatc tccgagatgc cttcagcaga gtgaagactt tctttcaaat gaaggatcag | 180 |
| ctggacaact tgttgttaaa ggagtccttg ctggaggact taagggtta cctgggttgc | 240 |
| caagccttgt ctgagatgat ccagttttac ctggaggagg tgatgcccca agctgagaac | 300 |
| caagacccag acatcaaggc gcatgtgaac tccctgggg agaacctgaa gaccctcagg | 360 |
| ctgaggctac ggcgctgtca tcgatttctt ccctgtgaaa acaagagcaa ggccgtggag | 420 |
| caggtgaaga atgcctttaa taagctccaa gagaaaggca tctacaaagc catgagtgag | 480 |
| tttgacatct tcatcaacta catagaagcc tacatgacaa tgaagatacg aaacggaagc | 540 |
| ggagctacta acttcagcct gctgaagcag gctggcgacg tggaggagaa ccctggacct | 600 |
| ggtctccggc cgatggaaat ctgcagaggc ctccgcagtc acctaatcac tctcctcctc | 660 |
| ttcctgttcc attcagagac gatctgccga ccctctggga aaaatccag caagatgcaa | 720 |
| gccttcagaa tctgggatgt taaccagaag accttctatc tgaggaacaa ccaactagtt | 780 |
| gccggatact tgcaaggacc aaatgtcaat ttagaagaaa agatagatgt ggtacccatt | 840 |
| gagcctcatg ctctgttctt gggaatccat ggagggaaga tgtgcctgtc ctgtgtcaag | 900 |
| tctggtgatg agaccagact ccagctggag gcagttaaca tcactgacct gagcgagaac | 960 |
| agaaagcagg acaagcgctt cgccttcatc cgctcagaca gtggccccac caccagtttt | 1020 |
| gagtctgccg cctgccccgg ttggttcctc tgcacagcga tggaagctga ccagcccgtc | 1080 |
| agcctcacca atatgcctga cgaaggcgtc atggtcacca aattctactt ccaggaggac | 1140 |
| gagtaggcta gcgtcgacgc caccatgcac agctcagcac tgctctgttg cctggtcctc | 1200 |
| ctgactgggg tgagggccag cccaggccag gcacccagt ctgagaacag ctgcacccac | 1260 |
| ttcccaggca acctgcctaa catgcttcga gatctccgag atgccttcag cagagtgaag | 1320 |
| actttctttc aaatgaagga tcagctggac aacttgttgt taaaggagtc cttgctggag | 1380 |
| gactttaagg gttacctggg ttgccaagcc ttgtctgaga tgatccagtt ttacctggag | 1440 |
| gaggtgatgc cccaagctga gaaccaagac ccagacatca aggcgcatgt gaactccctg | 1500 |

```
ggggagaacc tgaagaccct caggctgagg ctacggcgct gtcatcgatt tcttccctgt    1560
gaaaacaaga gcaaggccgt ggagcaggtg aagaatgcct taataagct ccaagagaaa    1620 ggcatctaca aagccatgag tgagtttgac atcttcatca actacataga agcctacatg    1680
acaatgaaga tacgaaacgg aagcggagct actaacttca gcctgctgaa gcaggctggc    1740
gacgtggagg agaaccctgg acctggtctc cggccgatgg aaatctgcag aggcctccgc    1800
agtcacctaa tcactctcct cctcttcctg ttccattcag agacgatctg ccgaccctct    1860
gggagaaaat ccagcaagat gcaagccttc agaatctggg atgttaacca agagccttc    1920 tatctgagga caaccaact agttgccgga tacttgcaag gaccaaatgt caatttagaa    1980
gaaaagatag atgtggtacc cattgagcct catgctctgt tcttgggaat ccatggaggg    2040
aagatgtgcc tgtcctgtgt caagtctggt gatgagacca gactccagct ggaggcagtt    2100
aacatcactg acctgagcga gaacagaaag caggacaagc gcttcgcctt catccgctca    2160
gacagtggcc ccaccaccag ttttgagtct gccgcctgcc ccggttggtt cctctgcaca    2220
gcgatggaag ctgaccagcc cgtcagcctc accaatatgc ctgacgaagg cgtcatggtc    2280
accaaattct acttccagga ggacgagtag gctag                              2315

<210> SEQ ID NO 12
<211> LENGTH: 614
<212> TYPE: DNA
<213> ORGANISM: Artificial Sequence
<220> FEATURE:
<223> OTHER INFORMATION: Synthetic

<400> SEQUENCE: 12
atgaactcct tctccacaag cgccttcggt ccagttgcct ctccctggg cctgctcctg      60 gtgttgcctg ctgccttccc tgccccagtc ttcacactcg aagatttcgt tggggactgg    120
cgacagacag ccggctacaa cctggaccaa gtccttgaac agggaggtgt gtccagtttg    180
tttcagaatc tcggggtgtc cgtaactccg atccaaagga ttgtcctgag cggtgaaaat    240
gggctgaaga tcgacatcca tgtcatcatc ccgtatgaag gtctgagcgg cgaccaaatg    300
ggccagatcg aaaaaatttt taaggtggtg taccctgtgg atgatcatca ctttaaggtg    360
atcctgcact atggcacact ggtaatcgac ggggttacgc cgaacatgat cgactatttc    420
ggacggccgt atgaaggcat cgccgtgttc gacggcaaaa agatcactgt aacagggacc    480
ctgtggaacg gcaacaaaat tatcgacgag cgcctgatca accccgacgg ctccctgctg    540
ttccgagtaa ccatcaacgg agtgaccggc tggcggctgt gcgaacgcat tctggcgtaa    600
ggccgcgact ctag                                                     614

<210> SEQ ID NO 13
<211> LENGTH: 34
<212> TYPE: DNA
<213> ORGANISM: Artificial Sequence
<220> FEATURE:
<223> OTHER INFORMATION: Synthetic

<400> SEQUENCE: 13
ataacttcgt atagcataca ttatacgaag ttat                                34

<210> SEQ ID NO 14
<211> LENGTH: 179
<212> TYPE: DNA
<213> ORGANISM: Artificial Sequence
<220> FEATURE:
```

<223> OTHER INFORMATION: Synthetic

<400> SEQUENCE: 14

| | | | | | |
|---|---|---|---|---|---|
| gtggaattat | cacctcgaga | ataaaatatc | tttattttca | ttacatctgt | gtgttggttt | 60 |
| tttgtgtgaa | tcgatagtac | taacatacgc | tctccatcaa | aacaaaacga | aacaaaacaa | 120 |
| actagcaaaa | taggctgtcc | ccagtgcaag | tgcaggtgcc | agaacatttc | tctctcgag | 179 |

<210> SEQ ID NO 15
<211> LENGTH: 6977
<212> TYPE: DNA
<213> ORGANISM: Artificial Sequence
<220> FEATURE:
<223> OTHER INFORMATION: Synthetic sequence

<400> SEQUENCE: 15

| | | | | | |
|---|---|---|---|---|---|
| cctgcaggca | gctgcgcgct | cgctcgctca | ctgaggccgc | ccgggcaaag | cccgggcgtc | 60 |
| gggcgacctt | tggtcgcccg | gcctcagtga | gcgagcgagc | gcgcagagag | ggagtggcca | 120 |
| actccatcac | tagggggttcc | tgcggccgca | cgcgtataac | ttcgtatagc | atacattata | 180 |
| cgaagttata | gatctaactt | gtttattgca | gcttataatg | gttacaaata | aggcaatagc | 240 |
| atcacaaatt | tcacaaataa | ggcatttttt | tcactgcatt | ctagttttgg | tttgtccaaa | 300 |
| ctcatcaatg | tatcttatca | tgtctggatc | tactcgagct | gcagtctaga | ctagcgcttg | 360 |
| aatttcgcgt | accgctctcg | cgcaatttcg | agtgtcgagt | tcctgacacg | ctcaaagcgt | 420 |
| tctttgtcct | tctgccatag | gctacgaaca | gcaagcccac | gcaccgaatt | gaatatcaac | 480 |
| caaaggatat | cttctgcatc | atcacgcgaa | agaccacggc | tcaccagaac | accaagccac | 540 |
| atatcctcga | cgacaaaccg | attcctctct | accgtgcgct | gaataccctc | gcgtaacgct | 600 |
| ggatcccggt | cggcagccac | aatcaaatca | aggctgatag | agaagtcatc | gtcgaggaaa | 660 |
| aattcggcgg | cgtcgtccag | catttgctgg | atgacgtcat | cctctggctt | caatttcgct | 720 |
| aatcgagccc | gactgcgttc | ggtgatctgt | tcgtaaagcc | attcaaaagt | ggcaagcaga | 780 |
| agctcaagct | ttgtcgggaa | atgatggctc | tgcgctcctc | tcgagacacc | tgcagcaccg | 840 |
| ggcacatctg | cgatccggaa | tcccgcgtaa | ccttttttccc | gtaaaacccc | cagggccgct | 900 |
| gcaatcaact | tgccctgggt | ctccattgcg | cgctctgcct | gtgttcttct | ctttggactc | 960 |
| atgaattcac | ctgcaggcca | gtaggcgccg | gtcacagctt | ggatctgtaa | cggcgcagaa | 1020 |
| cagaaaacga | aacaaagacg | tagagttgag | caagcagggt | caggcaaagc | gtggagagcc | 1080 |
| ggctgagtct | aggtaggctc | caagggagcg | ccggacaaag | gcccggtctc | gacctgagct | 1140 |
| ttaaacttac | ctagacggcg | gacgcagttc | aggaggcacc | acaggcggga | ggcggcagaa | 1200 |
| cgcgactcaa | ccggcgtgga | tggcggcctc | aggtagggcg | gcgggcgcgt | gaaggagaga | 1260 |
| tgcgagcccc | tcgaagcttc | agctgtgttc | tggcggcaaa | cccgttgcga | aaaagaacgt | 1320 |
| tcacggcgac | tactgcactt | atatacggtt | ctcccccacc | ctcgggaaaa | aggcggagcc | 1380 |
| agtacacgac | atcactttcc | cagtttaccc | cgcgccacct | tctctaggca | cccgttcaat | 1440 |
| tgccgacccc | tcccccaac | ttctcgggga | ctgtgggcga | tgtgcgctct | gcccactgac | 1500 |
| gggcaccgga | gcgatcgcag | atccgtggaa | ttatcacctc | gagaataaaa | tatctttatt | 1560 |
| ttcattacat | ctgtgtgttg | gttttttgtg | tgaatcgata | gtactaacat | acgctctcca | 1620 |
| tcaaaacaaa | acgaaacaaa | acaaactagc | aaaataggct | gtccccagtg | caagtgcagg | 1680 |
| tgccagaaca | tttctctctc | gagttcgaac | ctaggcgtta | cataacttac | ggtaaatggc | 1740 |
| ccgcctggct | gaccgcccaa | cgaccccgc | ccattgacgt | caataatgac | gtatgttccc | 1800 |

```
atagtaacgc caatagggac tttccattga cgtcaatggg tggagtattt acggtaaact   1860
gcccacttgg cagtacatca agtgtatcat atgccaagtc cgccccctat tgacgtcaat   1920
gacggtaaat ggcccgcctg gcattatgcc cagtacatga ccttacggga ctttcctact   1980
tggcagtaca tctacgtatt agtcatcgct attaccatgg tgatgcggtt ttggcagtac   2040
accaatgggc gtggatagcg gtttgactca cggggatttc caagtctcca ccccattgac   2100
gtcaatggga gtttgttttg gcaccaaaat caacgggact ttccaaaatg tcgtaataac   2160
cccgccccgt tgacgcaaat gggcaagctt gccgggtcga ggtaggcgtg tacggtggga   2220
ggcctatata agcaaccggt ataatacaaa cagaccagat tgtctgtttg ttcaattgga   2280
agaaggatcc tctgtcgacg ccaccatgta cagaatgcag ctgctgagct gtatcgccct   2340
gtctctggcc ctggtcacaa actctgccca cagccacaga acttccagc ctgtgctgca   2400 tctggtggcc ctgaactctc cactgtctgg cggcatgaga ggcatcagag gcgccgactt   2460
ccagtgtttc cagcaggcta gagctgtcgg cctggccgga acattcagag cctttctgag   2520
cagcagactg caggacctgt acagcatcgt gcggagagcc gatagagccg ctgtgcctat   2580
cgtgaacctg aaggacgagc tgctgttccc tagctgggaa gctctgttct ctggcagcga   2640
gggacctctg aaaccaggcg ccagaatctt cagcttcgac ggcaaggacg tgctgagaca   2700
ccctacctgg cctcagaaat ctgtgtggca cggcagcgat cccaacggca gaaggctgac   2760
agagagctac tgcgagactt ggaggacaga ggcccctagc gctacaggcc aagcaagctc   2820
acttctcgga ggcagactgc tgggacagtc tgccgcttct tgtcaccacg cctacatcgt   2880
gctgtgcatc gagaacagct tcatgaccgc cagcaaggtg ccaggcgtgg aacaaatag   2940 cgtgtacctg agcgagtgca agaccggcaa cggcaagaac tacagaggca ccatgagcaa   3000
gaccaagaac ggcatcacct gtcagaagtg gtccagcaca agccctcaca gacccagatt   3060
cagccctgct acacacccaa gcgaaggcct ggaagagaac tactgcagaa accccgacaa   3120 cgacccctcaa ggcccttggt gctacaccac cgatcctgag aagagatacg actactgcga   3180
catcctggaa tgcgaagagg aatgcatgca ctgcagcggc gagaactacg atggcaagat   3240
ctccaagacc atgagcggcc tcgagtgtca ggcctgggat tctcagtctc ctcacgctca   3300
cggctacatc cccagcaagt tccccaacaa gaatctgaag aagaattact gtcggaaccc   3360
cgaccgcgag ctgaggcctt ggtgtttcac aacagaccct aacaagagat gggagctgtg   3420
tgacatccct agatgcacca cacctccacc ttctagcggc cctacctacc agtgtctgaa   3480
aggcaccggc gagaattaca ggggcaatgt ggccgtgacc gtgtctggac acacatgcca   3540
acattggagc gcccagacac ctcacacaca aacagaacc cctgagaact tcccctgcaa   3600
gaacctggac gaaaactatt gccggaatcc tgacggcaag agggcccctt ggtgtcacac   3660
taccaacagc caagtccgct gggagtactg caagatcccc agctgtgaca gcagccctgt   3720
gtctacagaa cagctggccc ctacagctcc tcctgagctg acacctgtgg tgcaggactg   3780
ttatcacggc gacggccagt cctacagagg aacaagcagc accaccacaa ccggcaagaa   3840
gtgccagagc tggtctagca tgacccctca caggcaccag aaaacccag agaattaccc   3900 caacgccggc ctgaccatga actactgtag gaatccagac gccgacaaag cccctggtg   3960 ttttaccaca gatcccagcg tcagatggga atactgtaac ctgaagaagt gcagcggcac   4020
cgaggccagc gttgtgtgag ctagctggga tccagacatg ataagataca ttgatgagtt   4080 tggacaaaacc aaaactagaa tgcagtgaaa aaatgcctt atttgtgaaa tttgtgatgc   4140
```

```
tattgcctta tttgtaacca ttataagctg caataaacaa gttataactt cgtatagcat    4200
acattatacg aagttatcac gtgcggaccg agcggccgca ggaaccccta gtgatggagt    4260
tggccactcc ctctctgcgc gctcgctcgc tcactgaggc cgggcgacca aggtcgccc     4320 gacgcccggg ctttgcccgg gcggcctcag tgagcgagcg agcgcgcagc tgcctgcagg    4380
ggcgcctgat gcggtatttt ctccttacgc atctgtgcgg tatttcacac cgcatacgtc    4440
aaagcaacca tagtacgcgc cctgtagcgg cgcattaagc gcggcgggtg tggtggttac    4500
gcgcagcgtg accgctacac ttgccagcgc cctagcgccc gctcctttcg ctttcttccc    4560
ttcctttctc gccacgttcg ccggcttccc ccgtcaagct ctaaatcggg gctccctt      4620 agggttccga tttagtgctt tacggcacct cgaccccaaa aaacttgatt tgggtgatgg    4680
ttcacgtagt gggccatcgc cctgatagac ggttttttcgc cctttgacgt tggagtccac   4740
gttctttaat agtggactct tgttccaaac tggaacaaca ctcaacccta tctcgggcta    4800 ttctttgat ttataaggga ttttgccgat ttcggcctat tggttaaaaa atgagctgat     4860
ttaacaaaaa tttaacgcga attttaacaa aatattaacg tttacaattt tatggtgcac    4920
tctcagtaca atctgctctg atgccgcata gttaagccag ccccgacacc cgccaacacc    4980
cgctgacgcg ccctgacggg cttgtctgct cccggcatcc gcttacagac aagctgtgac    5040
cgtctccggg agctgcatgt gtcagaggtt ttcaccgtca tcaccgaaac gcgcgagacg    5100
aaagggcctc gtgatacgcc tatttttata ggttaatgtc atgataataa tggtttctta    5160
gacgtcaggt ggcacttttc ggggaaatgt gcgcggaacc cctatttgtt tattttttcta   5220 aatacattca aatatgtatc cgctcatgag acaataaccc tgataaatgc ttcaataata    5280
ttgaaaaagg aagagtatga gtattcaaca tttccgtgtc gcccttattc ccttttttgc    5340
ggcattttgc cttcctgttt ttgctcaccc agaaacgctg gtgaaagtaa agatgctga    5400 agatcagttg ggtgcacgag tgggttacat cgaactggat ctcaacagcg gtaagatcct    5460
tgagagtttt cgccccgaag aacgttttcc aatgatgagc acttttaaag ttctgctatg    5520
tggcgcggta ttatcccgta ttgacgccgg gcaagagcaa ctcggtcgcc gcatacacta    5580
ttctcagaat gacttggttg agtactcacc agtcacagaa aagcatctta cggatggcat    5640
gacagtaaga gaattatgca gtgctgccat aaccatgagt gataacactg cggccaactt    5700
acttctgaca acgatcggag gaccgaagga gctaaccgct tttttgcaca acatggggga    5760
tcatgtaact cgccttgatc gttgggaacc ggagctgaat gaagccatac caaacgacga    5820
gcgtgacacc acgatgcctg tagcaatggc aacaacgttg cgcaaactat taactggcga    5880
actacttact ctagcttccc ggcaacaatt aatagactgg atggaggcgg ataaagttgc    5940
aggaccactt ctgcgctcgg cccttccggc tggctggttt attgctgata atctggagc     6000 cggtgagcgt gggtctcgcg gtatcattgc agcactgggg ccagatggta agccctcccg    6060
tatcgtagtt atctacacga cggggagtca ggcaactatg gatgaacgaa atagacagat    6120
cgctgagata ggtgcctcac tgattaagca ttggtaactg tcagaccaag tttactcata    6180
tatactttag attgatttaa aacttcattt ttaatttaaa aggatctagg tgaagatcct    6240
ttttgataat ctcatgacca aaatccctta acgtgagttt tcgttccact gagcgtcaga    6300
ccccgtagaa aagatcaaag gatcttcttg agatcctttt tttctgcgcg taatctgctg    6360
cttgcaaaca aaaaaaccac cgctaccagc ggtggtttgt ttgccggatc aagagctacc    6420 aactctttt ccgaaggtaa ctggcttcag cagagcgcag ataccaaata ctgtccttct    6480
agtgtagccg tagttaggcc accacttcaa gaactctgta gcaccgccta catacctcgc    6540
```

```
tctgctaatc ctgttaccag tggctgctgc cagtggcgat aagtcgtgtc ttaccgggtt      6600
ggactcaaga cgatagttac cggataaggc gcagcggtcg ggctgaacgg ggggttcgtg      6660
cacacagccc agcttggagc gaacgaccta caccgaactg agatacctac agcgtgagct      6720
atgagaaagc gccacgcttc ccgaagggag aaaggcggac aggtatccgg taagcggcag      6780
ggtcggaaca ggagagcgca cgagggagct ccaggggga acgcctggt atctttatag        6840 tcctgtcggg tttcgccacc tctgacttga gcgtcgattt ttgtgatgct cgtcaggggg      6900
gcggagccta tggaaaaacg ccagcaacgc ggcctttta cggttcctgg ccttttgctg       6960
gccttttgct cacatgt                                                    6977

<210> SEQ ID NO 16
<211> LENGTH: 5819
<212> TYPE: DNA
<213> ORGANISM: Artificial Sequence
<220> FEATURE:
<223> OTHER INFORMATION: Synthetic

<400> SEQUENCE: 16
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac taggggttcc tgcggccgca cgcgtataac ttcgtatagc atacattata       180
cgaagttata gatctaactt gtttattgca gcttataatg gttacaaata aggcaatagc       240
atcacaaatt tcacaaataa ggcatttttt tcactgcatt ctagttttgg tttgtccaaa       300
ctcatcaatg tatcttatca tgtctggatc tactcgagct gcagtctaga ctagcgcttg       360
aatttcgcgt accgctctcg cgcaatttcg agtgtcgagt tcctgacacg ctcaaagcgt       420
tctttgtcct tctgccatag gctacgaaca gcaagcccac gcaccgaatt gaatatcaac       480
caaaggatat cttctgcatc atcacgcgaa agaccacggc tcaccagaac accaagccac       540
atatcctcga cgacaaaccg attcctctct accgtgcgct gaatacccctc gcgtaacgct       600 ggatcccggt cggcagccac aatcaaatca aggctgatag agaagtcatc gtcgaggaaa       660
aattcggcgg cgtcgtccag catttgctgg atgacgtcat cctctggctt caatttcgct       720
aatcgagccc gactgcgttc ggtgatctgt tcgtaaagcc attcaaaagt ggcaagcaga       780
agctcaagct ttgtcgggaa atgatggctc tgcgctcctc tcgagacacc tgcagcaccg       840
ggcacatctg cgatccggaa tcccgcgtaa cctttttccc gtaaaacccc cagggccgct       900
gcaatcaact tgccctgggt ctccattgcg cgctctgcct gtgttcttct ctttggactc       960
atgaattcac ctgcaggcca gtaggcgccg gtcacagctt ggatctgtaa cggcgcagaa      1020
cagaaaacga aacaaagacg tagagttgag caagcagggt caggcaaagc gtggagagcc      1080
ggctgagtct aggtaggctc caagggagcg ccggacaaag gcccggtctc gacctgagct      1140
ttaaacttac ctagcggcg gacgcagttc aggaggcacc acaggcggga ggcggcagaa       1200
cgcgactcaa ccggcgtgga tggcggcctc aggtagggcg gcgggcgcgt gaaggagaga      1260
tgcgagcccc tcgaagcttc agctgtgttc tggcggcaaa cccgttgcga aaagaacgt       1320 tcacggcgac tactgcactt atatacggtt ctcccccacc ctcgggaaaa aggcggagcc      1380
agtacacgac atcactttcc cagtttaccc cgcgccacct tctctaggca cccgttcaat      1440
tgccgacccc tcccccaac ttctcgggga ctgtgggcga tgtgcgctct gcccactgac       1500
gggcaccgga gcgatcgcag atccgtggaa ttatcacctc gagaataaaa tatctttatt      1560
```

-continued

```
ttcattacat ctgtgtgttg gttttttgtg tgaatcgata gtactaacat acgctctcca    1620
tcaaaacaaa acgaaacaaa acaaactagc aaaataggct gtccccagtg caagtgcagg    1680
tgccagaaca tttctctctc gagttcgaac ctaggcgtta cataacttac ggtaaatggc    1740
ccgcctggct gaccgcccaa cgaccccgc ccattgacgt caataatgac gtatgttccc     1800
atagtaacgc caatagggac tttccattga cgtcaatggg tggagtattt acggtaaact    1860
gcccacttgg cagtacatca agtgtatcat atgccaagtc cgcccccctat tgacgtcaat   1920
gacggtaaat ggcccgcctg gcattatgcc cagtacatga ccttacggga ctttcctact    1980
tggcagtaca tctacgtatt agtcatcgct attaccatgg tgatgcggtt ttggcagtac    2040
accaatgggc gtggatagcg gtttgactca cggggatttc caagtctcca ccccattgac    2100
gtcaatggga gtttgttttg gcaccaaaat caacgggact ttccaaaatg tcgtaataac    2160
cccgccccgt tgacgcaaat gggcaagctt gccgggtcga ggtaggcgtg tacggtggga    2220
ggcctatata agcaaccggt ataatacaaa cagaccagat tgtctgtttg ttcaattgga    2280
agaaggatcc tctgtcgacc tgagatcacc ggtagcatgc acagctcagc actgctctgt    2340
tgcctggtcc tcctgactgg ggtgagggcc agcccaggcc agggcaccca gtctgagaac    2400
agctgcaccc acttcccagg caacctgcct aacatgcttc gagatctccg agatgccttc    2460
agcagagtga agactttctt tcaaatgaag gatcagctgg acaacttgtt gttaaaggag    2520
tccttgctag aggactttaa gggttacctg ggttgccaag ccttgtctga gatgatccag    2580
ttttacctgg aggaggtgat gccccaagct gagaaccaag acccagacat caaggcgcat    2640
gtgaactccc tggggagaa cctgaagacc ctcaggctga ggctacggcg ctgtcatcga    2700
tttcttccct gtgaaaacaa gagcaaggcc gtggagcagg tgaagaatgc ctttaataag    2760
ctccaagaga aaggcatcta caaagccatg agtgagtttg acatcttcat caactacata    2820
gaagcctaca tgacaatgaa gatacgaaac tgagacatca gggtggcgac tctatagact    2880
cgctagctgg gatccagaca tgataagata cattgatgag tttggacaaa ccaaaactag    2940
aatgcagtga aaaaaatgcc ttatttgtga atttgtgat gctattgcct tatttgtaac    3000
cattataagc tgcaataaac aagttataac ttcgtatagc atacattata cgaagttatc    3060
acgtgcggac cgagcggccg caggaacccc tagtgatgga gttggccact ccctctctgc    3120
gcgctcgctc gctcactgag gccgggcgac caaaggtcgc ccgacgcccg ggctttgccc    3180
gggcggcctc agtgagcgag cgagcgcgca gctgcctgca ggggcgcctg atgcggtatt    3240
ttctccttac gcatctgtgc ggtatttcac accgcatacg tcaaagcaac catagtacgc    3300
gccctgtagc ggcgcattaa gcgcggcggg tgtggtggtt acgcgcagcg tgaccgctac    3360
acttgccagc gccctagcgc ccgctccttt cgctttcttc ccttcctttc tcgccacgtt    3420
cgccggcttt ccccgtcaag ctctaaatcg ggggctccct ttagggttcc gatttagtgc    3480
tttacggcac ctcgacccca aaaaacttga tttgggtgat ggttcacgta gtgggccatc    3540
gccctgatag acggtttttc gccctttgac gttggagtcc acgttcttta atagtggact    3600
cttgttccaa actggaacaa cactcaaccc tatctcgggc tattcttttg atttataagg    3660
gattttgccg atttcggcct attggttaaa aaatgagctg atttaacaaa atttaacgc     3720
gaatttaac aaaatattaa cgtttacaat tttatggtgc actctcagta caatctgctc     3780
tgatgccgca tagttaagcc agccccgaca cccgccaaca cccgctgacg cgccctgacg    3840
ggcttgtctg ctcccggcat ccgcttacag acaagctgtg accgtctccg ggagctgcat    3900
gtgtcagagg ttttcaccgt catcaccgaa acgcgcgaga cgaaagggcc tcgtgatacg    3960
```

| | | | | |
|---|---|---|---|---|
| cctattttta | taggttaatg | tcatgataat | aatggtttct | tagacgtcag gtggcacttt | 4020 |
| tcggggaaat | gtgcgcggaa | cccctatttg | tttattttc | taaatacatt caaatatgta | 4080 |
| tccgctcatg | agacaataac | cctgataaat | gcttcaataa | tattgaaaaa ggaagagtat | 4140 |
| gagtattcaa | catttccgtg | tcgcccttat | tccctttttt | gcggcatttt gccttcctgt | 4200 |
| ttttgctcac | ccagaaacgc | tggtgaaagt | aaaagatgct | gaagatcagt tgggtgcacg | 4260 |
| agtgggttac | atcgaactgg | atctcaacag | cggtaagatc | cttgagagtt ttcgccccga | 4320 |
| agaacgtttt | ccaatgatga | gcacttttaa | agttctgcta | tgtggcgcgg tattatcccg | 4380 |
| tattgacgcc | gggcaagagc | aactcggtcg | ccgcatacac | tattctcaga atgacttggt | 4440 |
| tgagtactca | ccagtcacag | aaaagcatct | tacggatggc | atgacagtaa gagaattatg | 4500 |
| cagtgctgcc | ataaccatga | gtgataacac | tgcggccaac | ttacttctga caacgatcgg | 4560 |
| aggaccgaag | gagctaaccg | cttttttgca | caacatgggg | gatcatgtaa ctcgccttga | 4620 |
| tcgttgggaa | ccggagctga | atgaagccat | accaaacgac | gagcgtgaca ccacgatgcc | 4680 |
| tgtagcaatg | gcaacaacgt | tgcgcaaact | attaactggc | gaactactta ctctagcttc | 4740 |
| ccggcaacaa | ttaatagact | ggatggaggc | ggataaagtt | gcaggaccac ttctgcgctc | 4800 |
| ggcccttccg | gctggctggt | ttattgctga | taaatctgga | gccggtgagc gtgggtctcg | 4860 |
| cggtatcatt | gcagcactgg | ggccagatgg | taagccctcc | cgtatcgtag ttatctacac | 4920 |
| gacggggagt | caggcaacta | tggatgaacg | aaatagacag | atcgctgaga taggtgcctc | 4980 |
| actgattaag | cattggtaac | tgtcagacca | agtttactca | tatatacttt agattgattt | 5040 |
| aaaacttcat | ttttaattta | aaaggatcta | ggtgaagatc | ctttttgata atctcatgac | 5100 |
| caaaatccct | taacgtgagt | tttcgttcca | ctgagcgtca | gacccgtag aaaagatcaa | 5160 |
| aggatcttct | tgagatcctt | ttttttctgcg | cgtaatctgc | tgcttgcaaa caaaaaaacc | 5220 |
| accgctacca | gcggtggttt | gtttgccgga | tcaagagcta | ccaactcttt ttccgaaggt | 5280 |
| aactggcttc | agcagagcgc | agataccaaa | tactgtcctt | ctagtgtagc cgtagttagg | 5340 |
| ccaccacttc | aagaactctg | tagcaccgcc | tacatacctc | gctctgctaa tcctgttacc | 5400 |
| agtggctgct | gccagtggcg | ataagtcgtg | tcttaccggg | ttggactcaa gacgatagtt | 5460 |
| accggataag | gcgcagcggt | cgggctgaac | ggggggttcg | tgcacacagc ccagcttgga | 5520 |
| gcgaacgacc | tacaccgaac | tgagatacct | acagcgtgag | ctatgagaaa gcgccacgct | 5580 |
| tcccgaaggg | agaaaggcgg | acaggtatcc | ggtaagcggc | agggtcggaa caggagagcg | 5640 |
| cacgagggag | cttccagggg | gaaacgcctg | gtatctttat | agtcctgtcg ggtttcgcca | 5700 |
| cctctgactt | gagcgtcgat | ttttgtgatg | ctcgtcaggg | gggcggagcc tatggaaaaa | 5760 |
| cgccagcaac | gcggcctttt | tacggttcct | ggccttttgc | tggccttttg ctcacatgt | 5819 |

<210> SEQ ID NO 17
<211> LENGTH: 248
<212> TYPE: PRT
<213> ORGANISM: Artificial Sequence
<220> FEATURE:
<223> OTHER INFORMATION: Synthetic

<400> SEQUENCE: 17

Met Ser Arg Leu Asp Lys Ser Lys Val Ile Asn Gly Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
             35                  40                  45

Arg Ala Leu Leu Asp Ala Leu Pro Ile Glu Met Leu Asp Arg His His
 50                  55                  60

Thr His Phe Cys Pro Leu Glu Gly Glu Ser Trp Gln Asp Phe Leu Arg
 65                  70                  75                  80

Asn Asn Ala Lys Ser Tyr Arg Cys Ala Leu Leu Ser His Arg Asp Gly
                 85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
            115                 120                 125

Asn Ala Leu Tyr Ala Leu Ser Ala Val Gly His Phe Thr Leu Gly Cys
130                 135                 140

Val Leu Glu Glu Gln Glu His Gln Val Ala Lys Glu Arg Glu Thr
145                 150                 155                 160

Pro Thr Thr Asp Ser Met Pro Pro Leu Leu Arg Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245

<210> SEQ ID NO 18
<211> LENGTH: 203
<212> TYPE: PRT
<213> ORGANISM: Artificial Sequence
<220> FEATURE:
<223> OTHER INFORMATION: Synthetic

<400> SEQUENCE: 18

Met Ser Pro Lys Arg Arg Thr Gln Ala Glu Arg Ala Met Glu Thr Gln
 1               5                  10                  15

Gly Lys Leu Ile Ala Ala Ala Leu Gly Val Leu Arg Glu Lys Gly Tyr
             20                  25                  30

Ala Gly Phe Arg Ile Ala Asp Val Pro Gly Ala Ala Gly Val Ser Arg
         35                  40                  45

Gly Ala Gln Ser His His Phe Pro Thr Lys Leu Glu Leu Leu Leu Ala
     50                  55                  60

Thr Phe Glu Trp Leu Tyr Glu Gln Ile Thr Glu Arg Ser Arg Ala Arg
 65                  70                  75                  80

Leu Ala Lys Leu Lys Pro Glu Asp Asp Val Ile Gln Gln Met Leu Asp
                 85                  90                  95

Asp Ala Ala Glu Phe Phe Leu Asp Asp Asp Phe Ser Ile Ser Leu Asp
            100                 105                 110

Leu Ile Val Ala Ala Asp Arg Asp Pro Ala Leu Arg Glu Gly Ile Gln
            115                 120                 125

Arg Thr Val Glu Arg Asn Arg Phe Val Val Glu Asp Met Trp Leu Gly
        130                 135                 140

```
Val Leu Val Ser Arg Gly Leu Ser Arg Asp Asp Ala Glu Asp Ile Leu
145                 150                 155                 160

Trp Leu Ile Phe Asn Ser Val Arg Gly Leu Ala Val Arg Ser Leu Trp
                165                 170                 175

Gln Lys Asp Lys Glu Arg Phe Glu Arg Val Arg Asn Ser Thr Leu Glu
            180                 185                 190

Ile Ala Arg Glu Arg Tyr Ala Lys Phe Lys Arg
            195                 200
```

<210> SEQ ID NO 19
<211> LENGTH: 178
<212> TYPE: PRT
<213> ORGANISM: Homo sapiens

<400> SEQUENCE: 19

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 20
<211> LENGTH: 577
<212> TYPE: PRT
<213> ORGANISM: Artificial Sequence
<220> FEATURE:
<223> OTHER INFORMATION: Synthetic

<400> SEQUENCE: 20

```
Met Tyr Arg Met Gln Leu Leu Ser Cys Ile Ala Leu Ser Leu Ala Leu
1               5                   10                  15

Val Thr Asn Ser Ala His Ser His Arg Asp Phe Gln Pro Val Leu His
            20                  25                  30

Leu Val Ala Leu Asn Ser Pro Leu Ser Gly Gly Met Arg Gly Ile Arg
        35                  40                  45

Gly Ala Asp Phe Gln Cys Phe Gln Gln Ala Arg Ala Val Gly Leu Ala
50                  55                  60

Gly Thr Phe Arg Ala Phe Leu Ser Ser Arg Leu Gln Asp Leu Tyr Ser
65                  70                  75                  80
```

```
Ile Val Arg Arg Ala Asp Arg Ala Ala Val Pro Ile Val Asn Leu Lys
                85                  90                  95

Asp Glu Leu Leu Phe Pro Ser Trp Glu Ala Leu Phe Ser Gly Ser Glu
                100                 105                 110

Gly Pro Leu Lys Pro Gly Ala Arg Ile Phe Ser Phe Asp Gly Lys Asp
                115                 120                 125

Val Leu Arg His Pro Thr Trp Pro Gln Lys Ser Val Trp His Gly Ser
    130                 135                 140

Asp Pro Asn Gly Arg Arg Leu Thr Glu Ser Tyr Cys Glu Thr Trp Arg
145                 150                 155                 160

Thr Glu Ala Pro Ser Ala Thr Gly Gln Ala Ser Ser Leu Leu Gly Gly
                165                 170                 175

Arg Leu Leu Gly Gln Ser Ala Ala Ser Cys His His Ala Tyr Ile Val
                180                 185                 190

Leu Cys Ile Glu Asn Ser Phe Met Thr Ala Ser Lys Val Pro Gly Val
    195                 200                 205

Gly Thr Asn Ser Val Tyr Leu Ser Glu Cys Lys Thr Gly Asn Gly Lys
    210                 215                 220

Asn Tyr Arg Gly Thr Met Ser Lys Thr Lys Asn Gly Ile Thr Cys Gln
225                 230                 235                 240

Lys Trp Ser Ser Thr Ser Pro His Arg Pro Arg Phe Ser Pro Ala Thr
                245                 250                 255

His Pro Ser Glu Gly Leu Glu Glu Asn Tyr Cys Arg Asn Pro Asp Asn
                260                 265                 270

Asp Pro Gln Gly Pro Trp Cys Tyr Thr Thr Asp Pro Glu Lys Arg Tyr
                275                 280                 285

Asp Tyr Cys Asp Ile Leu Glu Cys Glu Glu Cys Met His Cys Ser
                290                 295                 300

Gly Glu Asn Tyr Asp Gly Lys Ile Ser Lys Thr Met Ser Gly Leu Glu
305                 310                 315                 320

Cys Gln Ala Trp Asp Ser Gln Ser Pro His Ala His Gly Tyr Ile Pro
                325                 330                 335

Ser Lys Phe Pro Asn Lys Asn Leu Lys Lys Asn Tyr Cys Arg Asn Pro
                340                 345                 350

Asp Arg Glu Leu Arg Pro Trp Cys Phe Thr Thr Asp Pro Asn Lys Arg
                355                 360                 365

Trp Glu Leu Cys Asp Ile Pro Arg Cys Thr Thr Pro Pro Pro Ser Ser
    370                 375                 380

Gly Pro Thr Tyr Gln Cys Leu Lys Gly Thr Gly Glu Asn Tyr Arg Gly
385                 390                 395                 400

Asn Val Ala Val Thr Val Ser Gly His Thr Cys Gln His Trp Ser Ala
                405                 410                 415

Gln Thr Pro His Thr His Asn Arg Thr Pro Glu Asn Phe Pro Cys Lys
                420                 425                 430

Asn Leu Asp Glu Asn Tyr Cys Arg Asn Pro Asp Gly Lys Arg Ala Pro
                435                 440                 445

Trp Cys His Thr Thr Asn Ser Gln Val Arg Trp Glu Tyr Cys Lys Ile
    450                 455                 460

Pro Ser Cys Asp Ser Ser Pro Val Ser Thr Glu Gln Leu Ala Pro Thr
465                 470                 475                 480

Ala Pro Pro Glu Leu Thr Pro Val Val Gln Asp Cys Tyr His Gly Asp
                485                 490                 495
```

Gly Gln Ser Tyr Arg Gly Thr Ser Thr Thr Thr Gly Lys Lys
            500                 505                 510

Cys Gln Ser Trp Ser Ser Met Thr Pro His Arg His Gln Lys Thr Pro
        515                 520                 525

Glu Asn Tyr Pro Asn Ala Gly Leu Thr Met Asn Tyr Cys Arg Asn Pro
    530                 535                 540

Asp Ala Asp Lys Gly Pro Trp Cys Phe Thr Thr Asp Pro Ser Val Arg
545                 550                 555                 560

Trp Glu Tyr Cys Asn Leu Lys Lys Cys Ser Gly Thr Glu Ala Ser Val
                565                 570                 575

Val

<210> SEQ ID NO 21
<211> LENGTH: 177
<212> TYPE: PRT
<213> ORGANISM: Homo sapiens

<400> SEQUENCE: 21

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 22
<211> LENGTH: 34
<212> TYPE: DNA
<213> ORGANISM: Artificial Sequence
<220> FEATURE:
<223> OTHER INFORMATION: LoxP site

<400> SEQUENCE: 22
ataacttcgt atagcataca ttatacgaag ttat                                    34

<210> SEQ ID NO 23
<211> LENGTH: 34
<212> TYPE: DNA
<213> ORGANISM: Artificial Sequence
<220> FEATURE:
<223> OTHER INFORMATION: LoxP site

```
<400> SEQUENCE: 23
ataacttcgt ataatgtata ctatacgaag ttat                            34

<210> SEQ ID NO 24
<211> LENGTH: 34
<212> TYPE: DNA
<213> ORGANISM: Artificial Sequence
<220> FEATURE:
<223> OTHER INFORMATION: LoxP site

<400> SEQUENCE: 24
ataacttcgt ataatgtgta ctatacgaag ttat                            34

<210> SEQ ID NO 25
<211> LENGTH: 34
<212> TYPE: DNA
<213> ORGANISM: Artificial Sequence
<220> FEATURE:
<223> OTHER INFORMATION: LoxP site

<400> SEQUENCE: 25
ataacttcgt ataaagtatc ctatacgaag ttat                            34

<210> SEQ ID NO 26
<211> LENGTH: 34
<212> TYPE: DNA
<213> ORGANISM: Artificial Sequence
<220> FEATURE:
<223> OTHER INFORMATION: LoxP site

<400> SEQUENCE: 26
ataacttcgt ataagaaacc atatacgaag ttat                            34

<210> SEQ ID NO 27
<211> LENGTH: 34
<212> TYPE: DNA
<213> ORGANISM: Artificial Sequence
<220> FEATURE:
<223> OTHER INFORMATION: LoxP site

<400> SEQUENCE: 27
ataacttcgt atataatacc atatacgaag ttat                            34

<210> SEQ ID NO 28
<211> LENGTH: 34
<212> TYPE: DNA
<213> ORGANISM: Artificial Sequence
<220> FEATURE:
<223> OTHER INFORMATION: LoxP site

<400> SEQUENCE: 28
ataacttcgt ataagataga atatacgaag ttat                            34

<210> SEQ ID NO 29
<211> LENGTH: 34
<212> TYPE: DNA
<213> ORGANISM: Artificial Sequence
<220> FEATURE:
<223> OTHER INFORMATION: LoxP site

<400> SEQUENCE: 29
ataacttcgt ataagataga atatacgaag ttat                            34

<210> SEQ ID NO 30
```

```
<211> LENGTH: 34
<212> TYPE: DNA
<213> ORGANISM: Artificial Sequence
<220> FEATURE:
<223> OTHER INFORMATION: LoxP site
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 30
taccgttcgt atannntann ntatacgaag ttat                                  34

<210> SEQ ID NO 31
<211> LENGTH: 34
<212> TYPE: DNA
<213> ORGANISM: Artificial Sequence
<220> FEATURE:
<223> OTHER INFORMATION: LoxP site
<220> FEATURE:
<221> NAME/KEY: misc_feature
<222> LOCATION: (14)..(16)
<223> OTHER INFORMATION: n is a, c, g, or t
<220> FEATURE:
<221> NAME/KEY: misc_feature
<222> LOCATION: (19)..(21)
<223> OTHER INFORMATION: n is a, c, g, or t

<400> SEQUENCE: 31
ataacttcgt atannntann ntatacgaac ggta                                  34

<210> SEQ ID NO 32
<211> LENGTH: 34
<212> TYPE: DNA
<213> ORGANISM: Artificial Sequence
<220> FEATURE:
<223> OTHER INFORMATION: FRT site

<400> SEQUENCE: 32
gaagttccta ttctctagaa agtataggaa cttc                                  34

<210> SEQ ID NO 33
<211> LENGTH: 34
<212> TYPE: DNA
<213> ORGANISM: Artificial Sequence
<220> FEATURE:
<223> OTHER INFORMATION: FRT site

<400> SEQUENCE: 33
gaagttccta tactttctag agaataggaa cttc                                  34

<210> SEQ ID NO 34
<211> LENGTH: 34
<212> TYPE: DNA
<213> ORGANISM: Artificial Sequence
<220> FEATURE:
<223> OTHER INFORMATION: FRT site

<400> SEQUENCE: 34
agtgatttga tacttacatg agtaaaggaa ttag                                  34

<210> SEQ ID NO 35
<211> LENGTH: 34
<212> TYPE: DNA
<213> ORGANISM: Artificial Sequence
```

```
<220> FEATURE:
<223> OTHER INFORMATION: FRT site

<400> SEQUENCE: 35
gaagttccta tacttacatg agtaaaggaa ttag                                34

<210> SEQ ID NO 36
<211> LENGTH: 32
<212> TYPE: DNA
<213> ORGANISM: Artificial Sequence
<220> FEATURE:
<223> OTHER INFORMATION: rox site

<400> SEQUENCE: 36
taactttaaa taatgccaat tatttaaagt ta                                  32

<210> SEQ ID NO 37
<211> LENGTH: 32
<212> TYPE: DNA
<213> ORGANISM: Artificial Sequence
<220> FEATURE:
<223> OTHER INFORMATION: rox site

<400> SEQUENCE: 37
taactttaaa taaggccagt tatttaaagt ta                                  32

<210> SEQ ID NO 38
<211> LENGTH: 32
<212> TYPE: DNA
<213> ORGANISM: Artificial Sequence
<220> FEATURE:
<223> OTHER INFORMATION: rox site

<400> SEQUENCE: 38
taactttaaa taacgcctct tatttaaagt ta                                  32

<210> SEQ ID NO 39
<211> LENGTH: 32
<212> TYPE: DNA
<213> ORGANISM: Artificial Sequence
<220> FEATURE:
<223> OTHER INFORMATION: rox site

<400> SEQUENCE: 39
taactttaaa taaggcctgt tatttaaagt ta                                  32

<210> SEQ ID NO 40
<211> LENGTH: 32
<212> TYPE: DNA
<213> ORGANISM: Artificial Sequence
<220> FEATURE:
<223> OTHER INFORMATION: rox site

<400> SEQUENCE: 40
taactttaaa taaggcccgt tatttaaagt ta                                  32

<210> SEQ ID NO 41
<211> LENGTH: 32
<212> TYPE: DNA
<213> ORGANISM: Artificial Sequence
<220> FEATURE:
<223> OTHER INFORMATION: rox site

<400> SEQUENCE: 41
taactttaaa taaggccggt tatttaaagt ta                                  32
```

```
<210> SEQ ID NO 42
<211> LENGTH: 23
<212> TYPE: DNA
<213> ORGANISM: Artificial Sequence
<220> FEATURE:
<223> OTHER INFORMATION: att site

<400> SEQUENCE: 42
tcagcttttt tatactaagt tgg                                              23

<210> SEQ ID NO 43
<211> LENGTH: 23
<212> TYPE: DNA
<213> ORGANISM: Artificial Sequence
<220> FEATURE:
<223> OTHER INFORMATION: att site

<400> SEQUENCE: 43
cctgcttttt tatactaact tga                                              23

<210> SEQ ID NO 44
<211> LENGTH: 23
<212> TYPE: DNA
<213> ORGANISM: Artificial Sequence
<220> FEATURE:
<223> OTHER INFORMATION: att site

<400> SEQUENCE: 44
tgcgctaatt tatacgaggc tac                                              23

<210> SEQ ID NO 45
<211> LENGTH: 23
<212> TYPE: DNA
<213> ORGANISM: Artificial Sequence
<220> FEATURE:
<223> OTHER INFORMATION: att site

<400> SEQUENCE: 45
gcgtaatgtt tataaatggc ggc                                              23

<210> SEQ ID NO 46
<211> LENGTH: 23
<212> TYPE: DNA
<213> ORGANISM: Artificial Sequence
<220> FEATURE:
<223> OTHER INFORMATION: att site

<400> SEQUENCE: 46
cgcctttgtt ttcaaaaacc tgc                                              23

<210> SEQ ID NO 47
<211> LENGTH: 23
<212> TYPE: DNA
<213> ORGANISM: Artificial Sequence
<220> FEATURE:
<223> OTHER INFORMATION: att site

<400> SEQUENCE: 47
cgggcttttt tctgtgtttc ctg                                              23
```

```
<210> SEQ ID NO 48
<211> LENGTH: 23
<212> TYPE: DNA
<213> ORGANISM: Artificial Sequence
<220> FEATURE:
<223> OTHER INFORMATION: att site

<400> SEQUENCE: 48
ttggctattt taccacgact gtc                                              23
```

EXPRESSION VECTOR AND METHOD

CROSS-REFERENCE TO RELATED APPLICATIONS

This application is a U.S. National Phase Application of Int'l Appl. No. PCT/AU2019/050046, filed Jan. 23, 2019, which claims priority to Int'l Appl. No. AU 2018900206, filed Jan. 23, 2018, each of which is incorporated herein by reference.

SEQUENCE LISTING DISCLOSURE

This application includes a sequence listing which has been submitted via EFS-Web in a file named "2953220o001000.txt" created Jan. 8, 2021, and having a size of 50,950 bytes, which is hereby incorporated by reference in its entirety.

FIELD OF THE INVENTION

The present disclosure relates to regulatable expression vectors for systematically controlling and silencing expression of a therapeutic molecule and uses thereof, e.g. treating ocular disorders such as choroidal neovascularisation.

BACKGROUND OF THE INVENTION

Gene delivery using viral vectors can result in long-term sustained transgene expression in the eye. However, technological improvements are required in order to move current systems into clinical practice. One issue is the ability to modulate transgene expression. Control should be maintained both temporally and quantitatively to avoid aberrant production of therapeutic. Moreover, certain diseases have a narrow therapeutic window, thus treatments must not only be specific, but timely. Incorporation of cell-specific regulating elements may aid in this process; however, such elements have not been identified in all ocular cell types, and those that have been identified are generally quite large, exceeding the size constraints of viral vectors with limited cargo capacities.

New expression vectors and methods for regulated gene delivery are therefore required.

SUMMARY OF THE INVENTION

Regulating or silencing expression of therapeutic genes in the eye may be necessary if their action leads to unexpected or unwanted effects. Accordingly, the present inventors have developed regulatable expression vectors for systematically controlling and silencing expression of a therapeutic molecule.

In a first example, the present disclosure encompasses an expression vector comprising a kill switch and a regulatable element operably linked to a nucleic acid sequence encoding a therapeutic molecule, wherein activity of the regulatable element is regulated by a regulator compound, and wherein activation of the kill switch silences expression of the nucleic acid encoding the therapeutic molecule from the vector.

In one example, the the kill switch comprises a first site-specific recombination sequence and a second site-specific recombination sequence, wherein recombination between the first site-specific recombination sequence and the second site-specific recombination sequence silences expression of the therapeutic molecule.

In one example, the first site-specific recombination sequence is positioned upstream of the nucleic acid sequence encoding the therapeutic molecule and the second site-specific recombination sequence is positioned downstream of the nucleic acid sequence encoding the therapeutic molecule.

In one example, the first site-specific recombination sequence and the second site-specific recombination sequence are loxP sites.

In one example, the expression vector further comprises a constitutive promoter operably linked to a nucleic acid sequence encoding a regulator compound-binding polypeptide which is capable of binding a regulator compound, wherein upon binding the regulator compound, the regulator compound-binding polypeptide regulates expression of the therapeutic molecule.

In one example, upon binding of the regulator compound, the regulator compound-binding polypeptide promotes expression of the therapeutic molecule.

In one example, upon binding of the regulator compound, the regulator compound-binding polypeptide represses expression of the therapeutic molecule.

In one example, the regulator compound-binding polypeptide comprises one or more of a reverse tetracycline-controlled transactivator (rtTA), a tetracycline-controlled transactivator (tTA) or a cysteine metabolism repressor (CymR).

In an example, the regulator compound-binding polypeptide comprises an amino acid sequence set forth in SEQ ID NO: 17 or SEQ ID NO: 18.

In one example, the regulator compound is tetracycline, cumate, progesterone, a glucocorticoid, estrogen, or mifepristone.

In one example, the regulatable element comprises one or more of a tetracycline responsive element (TRE), a cumate operator (CuO), an ecdysone response element (EcRE), estrogen response element (ERE), a glucocorticoid response element (GRE), a progesterone response element (PRE), a heat shock sequence element (HSE), or a light inducible promoter.

In one example, the regulatable element comprises a nucleic acid sequence set forth in SEQ ID NO: 4 or SEQ ID NO: 5.

In one example, the constitutive promoter is a composite human CMV-EF1-HTLV promoter.

In one example, the constitutive promoter comprises a nucleic acid sequence set forth in SEQ ID NO: 6.

In one example, the therapeutic molecule inhibits angiogenesis.

In one example, the therapeutic molecule inhibits inflammation.

In one example, the therapeutic molecule is a nucleic acid or polypeptide. In one example, the therapeutic molecule is a polypeptide.

In one example, the therapeutic molecule:
comprises endostatin, angiostatin, or a fusion of endostatin and angiostatin;
is a binding protein;
comprises an antigen binding site of an antibody;
is selected from the group consisting of ranibizumab, bevacizumab, and aflibercept;
inhibits inflammation; or,
is interleukin 10 (IL-10), interleukin 1 receptor antagonist (IL-1RA); or a fusion of IL-10 and IL-1RA.

In one example, the expression vector further comprises a transcription blocker between the constitutive promoter and the regulatable promoter.

In one example, the expression vector comprises
a first loxP site positioned upstream of the nucleic acid sequence encoding the therapeutic molecule and a second loxP site positioned downstream of the nucleic acid sequence encoding the therapeutic molecule,
a regulatable promoter comprising a tetracycline responsive element operably linked to the nucleic acid sequence encoding the therapeutic molecule, and
a constitutive promoter operably linked to a nucleic acid sequence encoding a reverse tetracycline-controlled transactivator (rtTA).

In one example, the expression vector is a viral vector. In one example, the expression vector is an adeno-associated virus (AAV) vector.

The present inventors have also identified that the vectors disclosed herein appear to be particularly effective at regulating inflammatory pathways and/or angiogenesis. These findings indicate that the expression vectors of the present disclosure may be useful for treating ocular disorders. Therefore, in another example, the present disclosure encompasses a method of treating an ocular disorder in a subject, the method comprising administering an effective amount of an expression vector which comprises a kill switch and a nucleic acid encoding a therapeutic molecule, wherein activation of the kill switch silences expression of the therapeutic molecule.

In one example, the expression vector further comprises a regulatable element operably linked to the nucleic acid encoding the therapeutic molecule, wherein the activity of the regulatable element is regulated by administration of a regulator compound to the subject.

In one example, the method described herein further comprises administering a second expression vector which comprises a constitutive promoter operably linked to a nucleic acid sequence encoding a regulator compound-binding polypeptide which is capable of binding a regulator compound, wherein upon binding the regulator compound, the regulator compound-binding polypeptide regulates expression of the therapeutic molecule from the first expression vector.

In one example, the expression vector further comprises a constitutive promoter operably linked to a nucleic acid sequence encoding a regulator compound-binding polypeptide which binds the regulator compound, wherein upon binding the regulator compound, the regulator compound-binding polypeptide regulates expression of the therapeutic molecule.

In one example, upon binding the regulator compound, the regulator compound-binding polypeptide promotes expression of the therapeutic molecule.

In one example, upon binding the regulator compound, the regulator compound-binding polypeptide represses expression of the therapeutic molecule.

In one example, activation of the kill switch excises:
one or more promoters; and/or,
the nucleic acid encoding the therapeutic molecule.

In one example, the kill switch comprises site-specific recombination sequences which flank:
one or more promoters; and/or
the nucleic acid encoding a therapeutic molecule.

In one example, the method further comprises administering an expression vector as defined herein.

In one example, the ocular disorder is diabetic retinopathy, cystoid macular oedema, clinically significant macular oedema, uveitis, iritis, giant cell arteritis, vasculitis, pars planitis, corneal transplant rejection, intraocular inflammation or lamellar corneal transplant rejection.

In one example, the ocular disorder is a cancer. In one example, the cancer is uveal melanoma.

In one example, the ocular disorder is macular degeneration, diabetic retinopathy, cystoid macular oedema, clinically significant macular oedema, central retinal vein occlusion, branch retinal vein occlusion or ocular neovascularisation.

In one example, the method described herein comprises intravitreal or subretinal administration of the expression vector.

Current treatment of various ocular disorders disclosed herein requires continual administration of therapeutic via invasive intravitreal injection. Along with being generally unpleasant, intravitreal administration of therapeutic is not without risk of infection or other side effect. One advantage of the vectors disclosed herein is their capacity for non-invasive regulation. For example, while vectors disclosed herein may be initially administered via intravitreal or subretinal injection, they may be subsequently regulated by topical or oral administration of regulator compound(s). For example, the regulator compound may be administered as an eye drop formulation. Accordingly, in another example, the methods described herein further comprise administering the regulator compound to the eye topically.

In one example, the regulator compound is a small molecule.

In one example, the regulator compound is tetracycline or cumate.

In one example, the regulator compound is administered in eye drops.

In one example, the method described herein further comprises activating the kill switch by administering a site-specific recombinase or a nucleic acid encoding a site-specific recombinase, wherein the site-specific recombinase catalyses the recombination between a first site-specific recombination sequence and the second site-specific recombination sequence, thereby silencing expression of the therapeutic molecule.

In another example, the present disclosure encompasses a method of treating an ocular disorder in a subject, the method comprising administering an effective amount of an expression vector, the expression vector comprising a kill switch, a nucleic acid encoding a therapeutic molecule, a regulatable promoter operably linked to the nucleic acid encoding the therapeutic molecule and a constitutive promoter operably linked to a nucleic acid sequence encoding a regulator compound-binding polypeptide, wherein the activity of the regulatable promoter is regulated by the regulator compound-binding polypeptide following administration of a regulator compound to the subject and wherein, activation of the kill switch silencing expression of the therapeutic molecule.

In another example, the present disclosure encompasses an expression vector defined herein for use in treating an ocular disorder in a subject. In another example, the present disclosure encompasses use of an expression vector defined herein in the manufacture of a medicament for the treatment of an ocular disorder.

In another example, the present disclosure encompasses a pharmaceutical composition comprising a first expression vector as defined herein and a second expression vector which comprises a constitutive promoter operably linked to a nucleic acid sequence encoding a regulator compound-binding polypeptide which is capable of binding a regulator compound, wherein upon binding the regulator compound, the regulator compound-binding polypeptide regulates expression of the therapeutic molecule from the first expression vector.

In another example, the present disclosure encompasses a kit comprising an expression vector(s) defined herein and an eye drop formulation comprising a regulator compound(s) defined herein. In one example, the kit comprises a therapeutic system.

In one example, the kit further comprises a kill switch activator as defined herein.

In one example, the kit further comprises an expression vector comprising a nucleic acid sequence encoding a kill switch activator as defined herein.

In one example, the kit comprises
an expression vector(s) defined herein,
an eye drop formulation comprising tetracycline, and
a Cre recombinase or an expression vector comprising a nucleic acid sequence encoding a Cre recombinase.

Any example herein shall be taken to apply mutatis mutandis to any other example unless specifically stated otherwise.

The present disclosure is not to be limited in scope by the specific examples described herein, which are intended for the purpose of exemplification only. Functionally-equivalent products, compositions and methods are clearly within the scope of the disclosure, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The disclosure is hereinafter described by way of the following non-limiting Examples and with reference to the accompanying drawings.

BRIEF DESCRIPTION OF THE ACCOMPANYING DRAWINGS

FIG. 1. Map of the backbone of a kill switch vector. It is a bi-cistronic vector encoding a repressor cloning site driven by the composite human CMV-EF1-HTLV promoter and cloning sites for a promoter and gene of interest. The promoter sites are separated by a transcription blocker. The construct is flanked by two AAV2 ITR sequences to package into AAV, and LoxP sites allowing controlled excision and killing of the vector.

Figure 2:
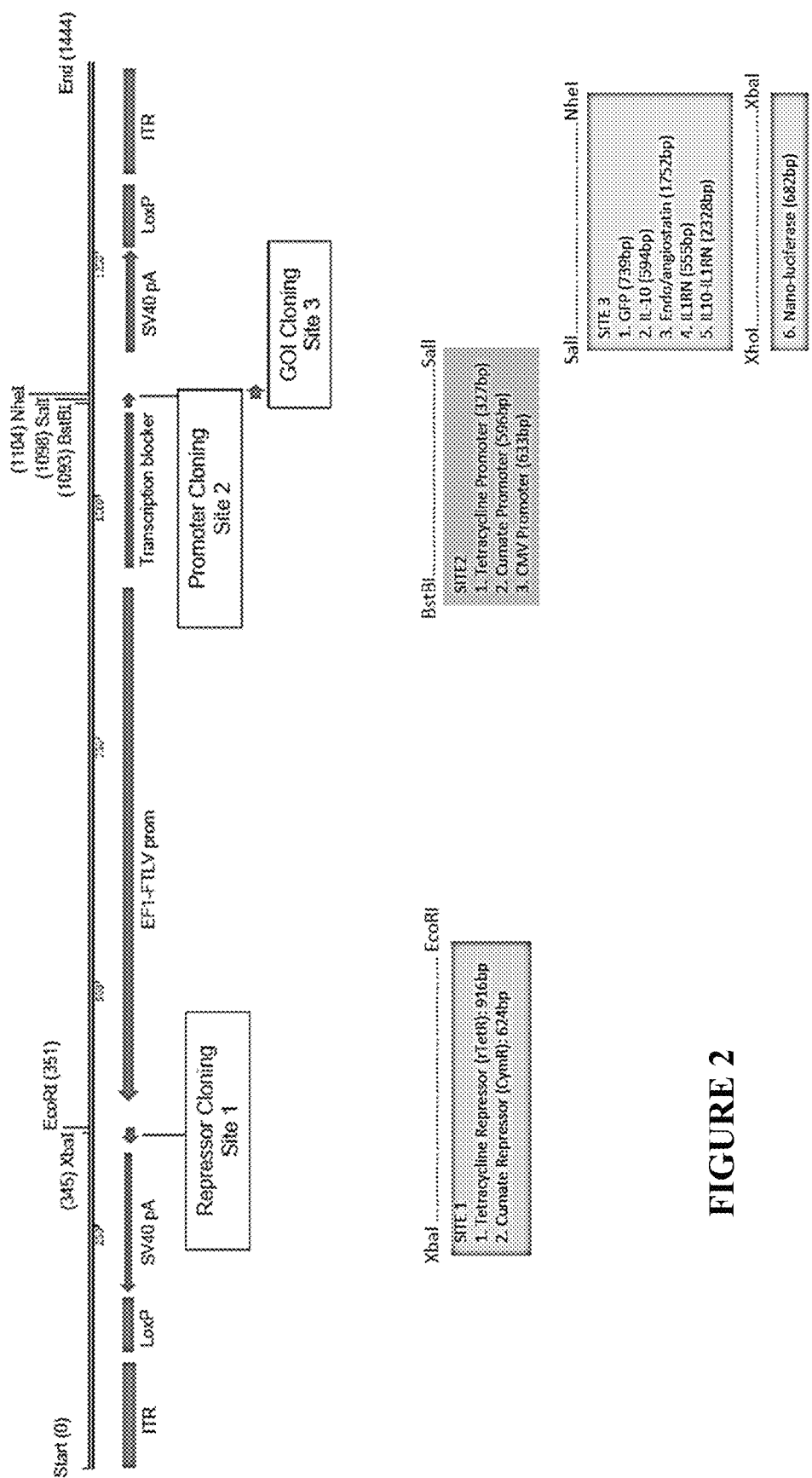

FIG. 2. Schematic of vector construction. Tetracycline or cumate repressor genes (SEQ ID NO: 2 and SEQ ID NO: 3 respectively) were cloned into the repressor cloning site 1 using XbaI and EcoRI restriction sites. The corresponding promoter (SEQ ID NO: 4 and SEQ ID NO: 5 respectively) was cloned into promoter cloning site 2 using BstBI and SalI restriction sites. The conditionally regulated gene of interest was cloned into the GOI cloning site 3 using SalI and NheI restriction sites (e.g., GFP, IL-10, Endo/Angiostation fusion protein, IL1RN or IL10/IL1RN genes set forth in SEQ ID NO: 7 to 11) or the compatible XhoI and XbaI sites (Nano-Luciferase, SEQ ID NO: 12).

Figure 3:
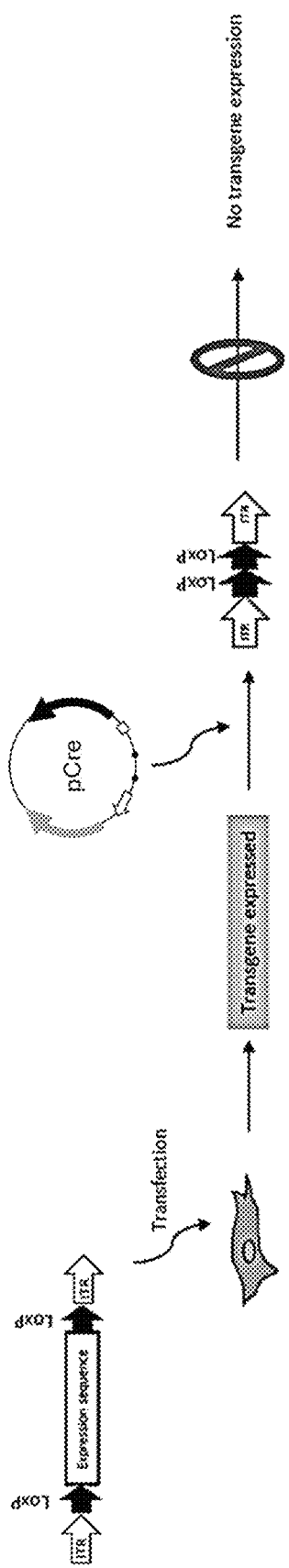

FIG. 3. Schematic of the mechanism of the kill switch. The vector has been constructed with all expression sequences located within 2 LoxP sites (SEQ ID NO: 13). This configuration allows expression to occur. In order to permanently stop or kill expression, a vector encoding Cre is added to the cells. Cre removes all expression sequences by splicing at the two lox sites. As a result, the vector is absent of expression machinery and cannot induce transgene expression.

Figure 4:
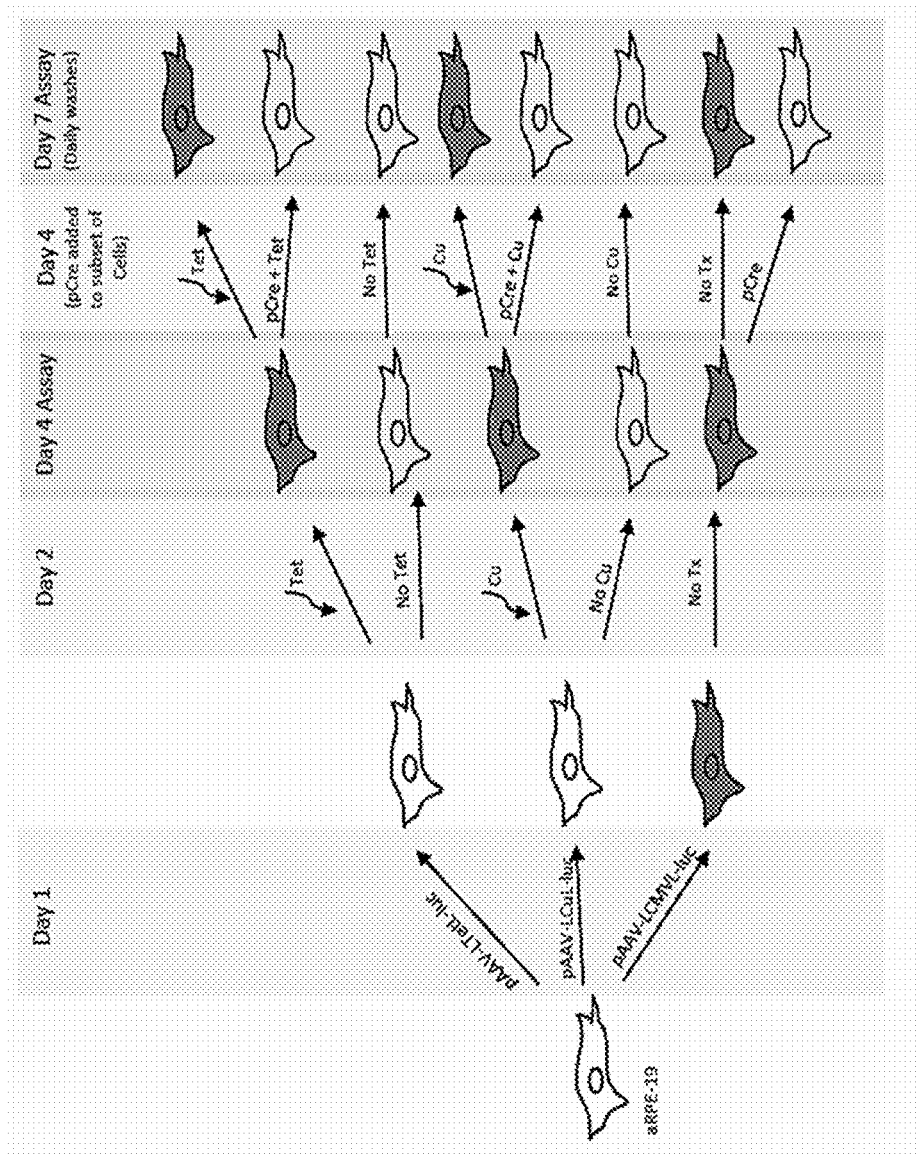

FIG. 4. Experimental design used for testing the kill switch in the vector constructs. A human retinal pigmented epithelial cell line (aRPE-19) was transfected with vector constructs containing Tet or Cu regulatory sequences or CMV, driving the expression of the marker gene luciferase. Twenty-four hours later, the cells were treated with or without Tet or Cu and incubated for a further 48 hours before assessing the expression of luciferase. The ability of the system to kill expression of the transgene (Luciferase) was examined by transfecting a Cre vector into the cells to cut out the expression sequences between LoxP sites. The cells are washed and drugs added back daily until day 7 when media is assayed for changes in expression levels of luciferase.

Figure 5:
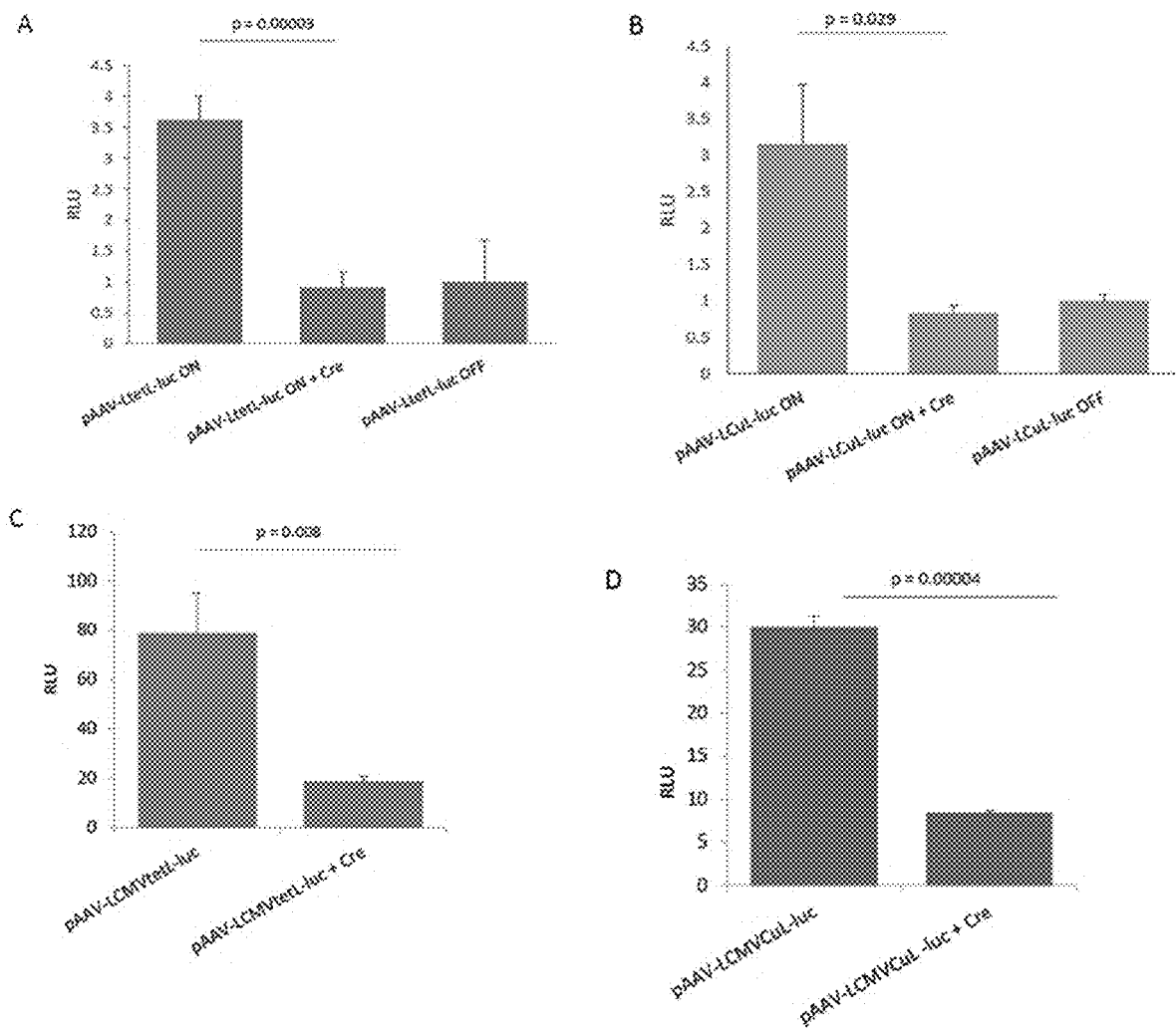

FIG. 5. Experimental results obtained from testing the kill switch. FIG. 5A shows the expression of luciferase in cells treated with the Tet vector with (pAAV-LTetL-luc ON) or without (pAAV-LTetL-luc OFF) Tet activation. Activated cells were then treated with Cre and luciferase assayed. FIG. 5B shows the expression of luciferase in cells treated with the Cu vector with or without Cu activation. Cells with activated Cu promoters were treated with Cre and luciferase expression assayed. FIG. 5C and FIG. 5D show the expression of luciferase following transfection with CMV vectors, with or without Cre mediated excision respectively. Significantly less luciferase expression was detected in all Cre excised cells.

Figure 6A:
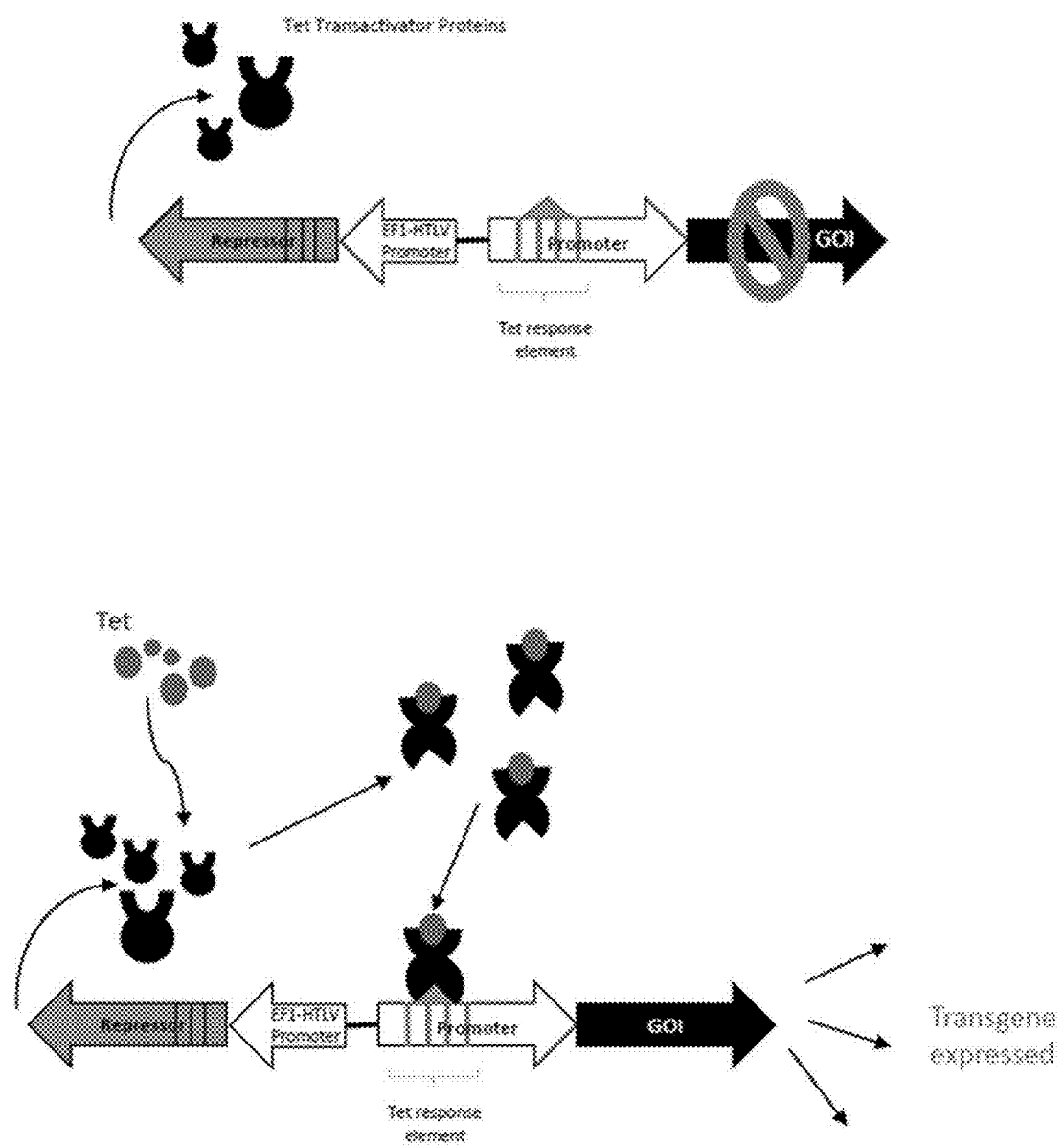
Figure 6B:
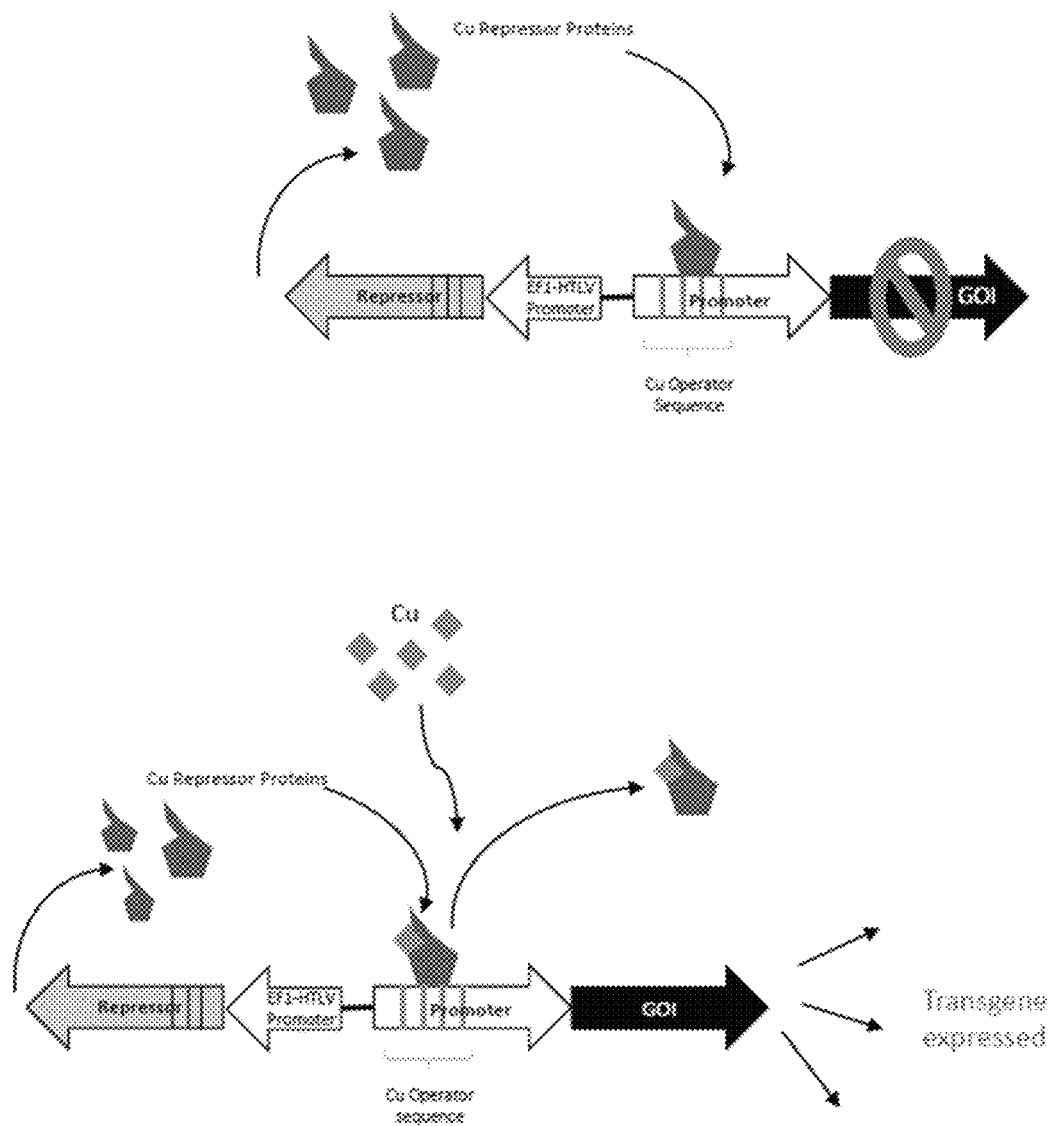

FIG. 6. Schematic of the controlled expression provided by the vector system. FIG. 6A shows the Tet On system. The EF1-HTLV promoter constituently expresses Tet transactivator proteins that are unable to bind to Tet responsive elements (TRE) in the Tet promoter resulting in its inactivation and the lack of transgene expression. In the presence of Tetracycline, the transactivator proteins bind to the Tet Response Elements (TRE) in the promoter, activating it and inducing the expression of the transgene. FIG. 6B shows the Cu On system. In this system, the Cu repressor protein binds to the Cu operator sequence in the absence of Cu, thus inactivating the promoter resulting in no transgene transcription. With the addition of Cu, the Cu binds to the repressor protein, bound to the Cu promoter, thus releasing the repressor allowing transgene transcription.

Figure 7:
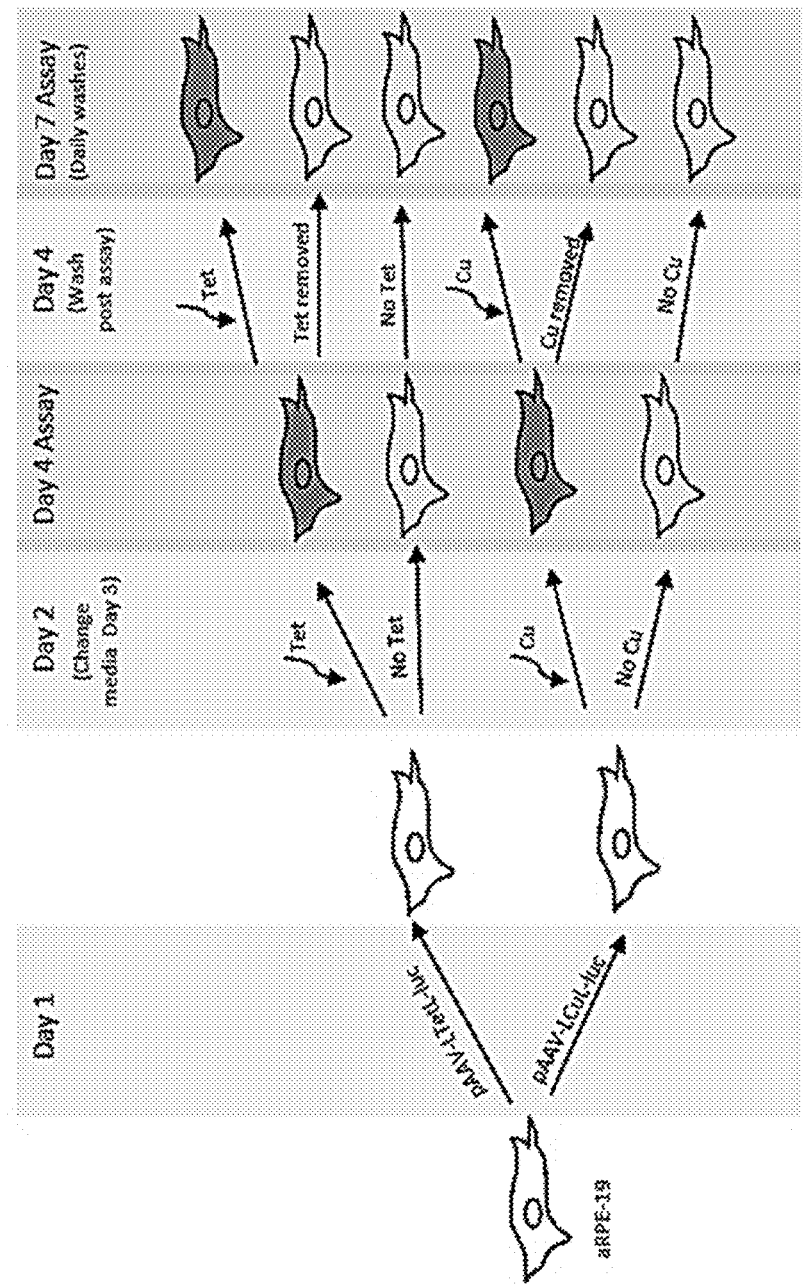

FIG. 7. Schematic of the experimental design used to test the ability of the vector constructs to regulate transgene expression. A human retinal pigmented epithelial cell line (aRPE-19) was transfected with vector constructs containing Tet or Cu regulatory sequences driving the expression of the marker gene luciferase. Twenty-four hours later, the cells were treated with or without Tet or Cu and incubated for a further 48 hours before assessing the expression of luciferase. The ability of the system to stop expression of the transgene (Luciferase) was examined by removing the Tet or Cu from the cells by washing prior to re-examining Luciferase expression. Cells without Tet or Cu were used as a control as were cells where Tet or Cu was not removed.

Figure 8:
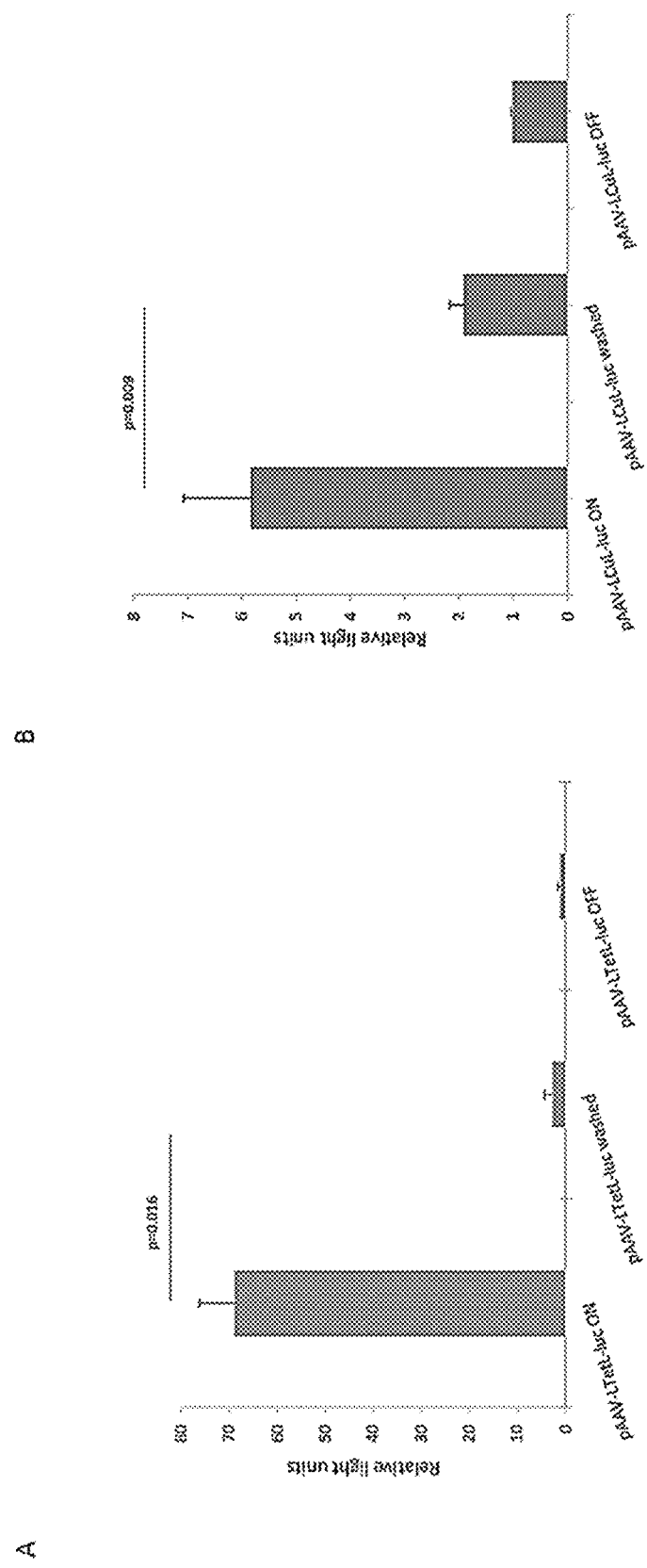

FIG. 8. Regulated gene expression using vector constructs. FIG. 8A shows the results from a luminescence assay performed on day 7 of the experiment using tetracycline as the agent to switch on transgene production. FIG. 8B shows the results from a luminescence assay performed on day 7 of the experiment using cumate as the agent to switch on transgene production. In both experiments, the substrate (Tet or Cu) was able to induce significant levels of luciferase and expression could be regulated by the removal of the substrate resulting in significantly less luciferase detected.

Figure 9:
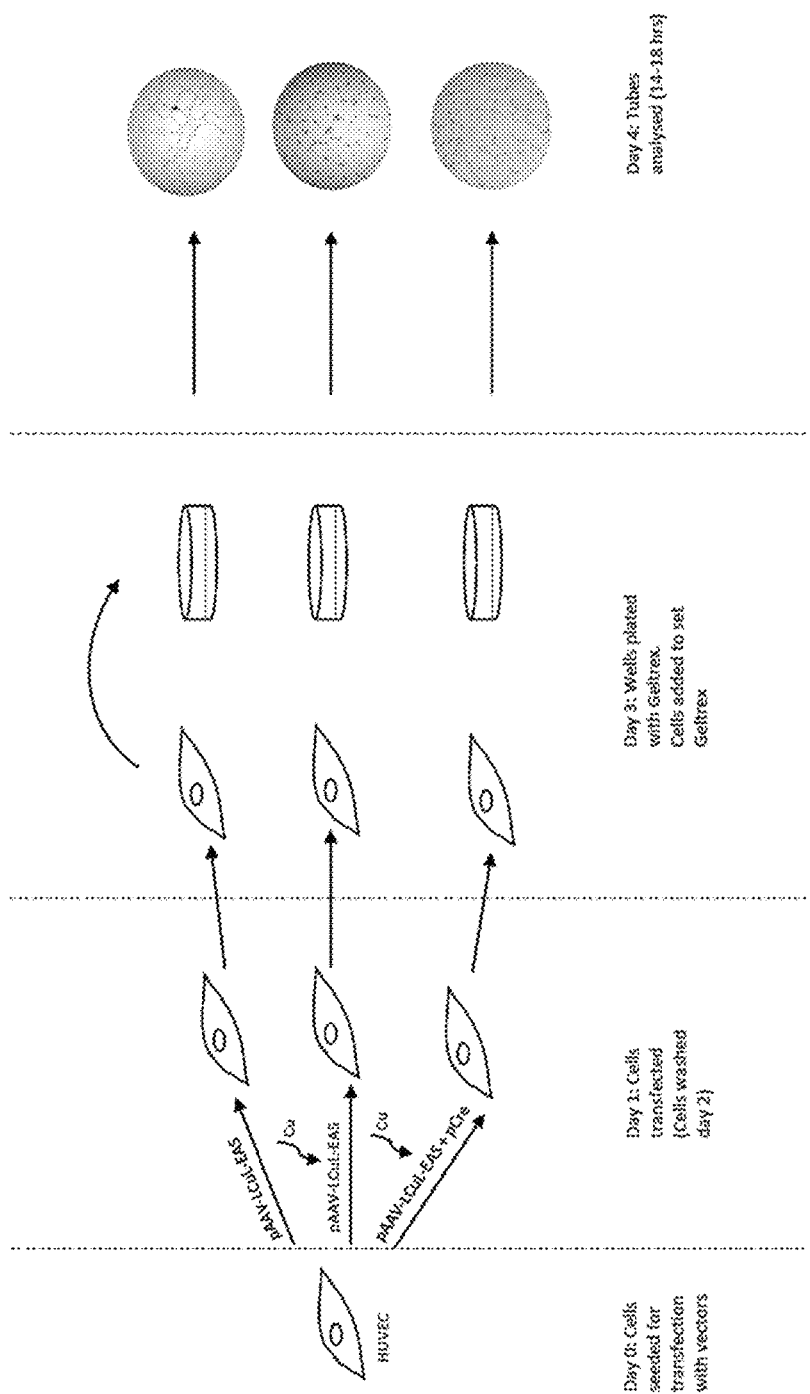

FIG. 9. Schematic of the experimental design used to examine the effects of a vector containing an endo/angiostatin fusion (EAS) flanked by LoxP sites on angiogenesis using a tube formation assay with primary human umbilical vein epithelial cells (HUVEC), with or without Cre. Early passage (p2-4) HUVECs were transfected with the cumate regulated vector producing EAS (pAAV-LCuL-EAS). Two days post transfection, cells were counted and seeded in geltrex coated wells and incubated at 370C, 5% CO2 for 14-18 hours after which the tubes formed in the geltrex were photographed and analysed using ImageJ angiogenesis analyser.

Figure 10:
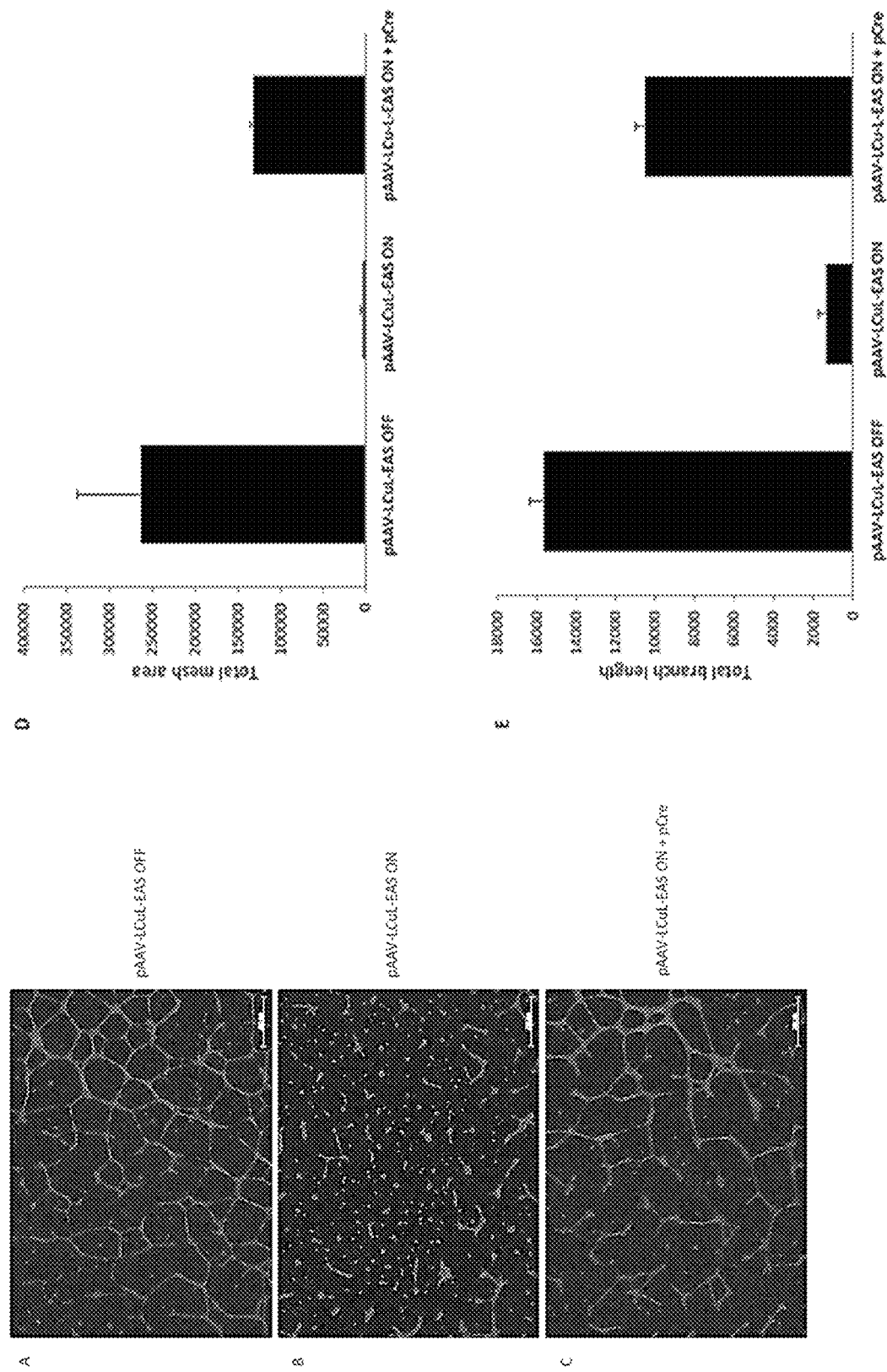

FIG. 10. Results obtained from testing the effects of EAS on the formation of tubules in HUVECs. FIG. 10A shows HUVEC tube formation in cells transfected with the non-EAS expressing pAAV-LCuL-EAS without Cu activation. FIG. 10B shows the inhibition of tube formation when HUVECs were treated with activated pAAV-LCuL-EAS. FIG. 10C shows the return of tube formation capacity when the activated pAAV-LCuL-EAS was excised by Cre. FIGS. 10D and 10E quantifies the total mesh area and total branch length respectively using ImageJ Angiogenesis Analyzer software. The pAAV-LCuL-EAS vector was able to reduce tube formation, which was largely reversed when the vector was excised by Cre.

Figure 11:
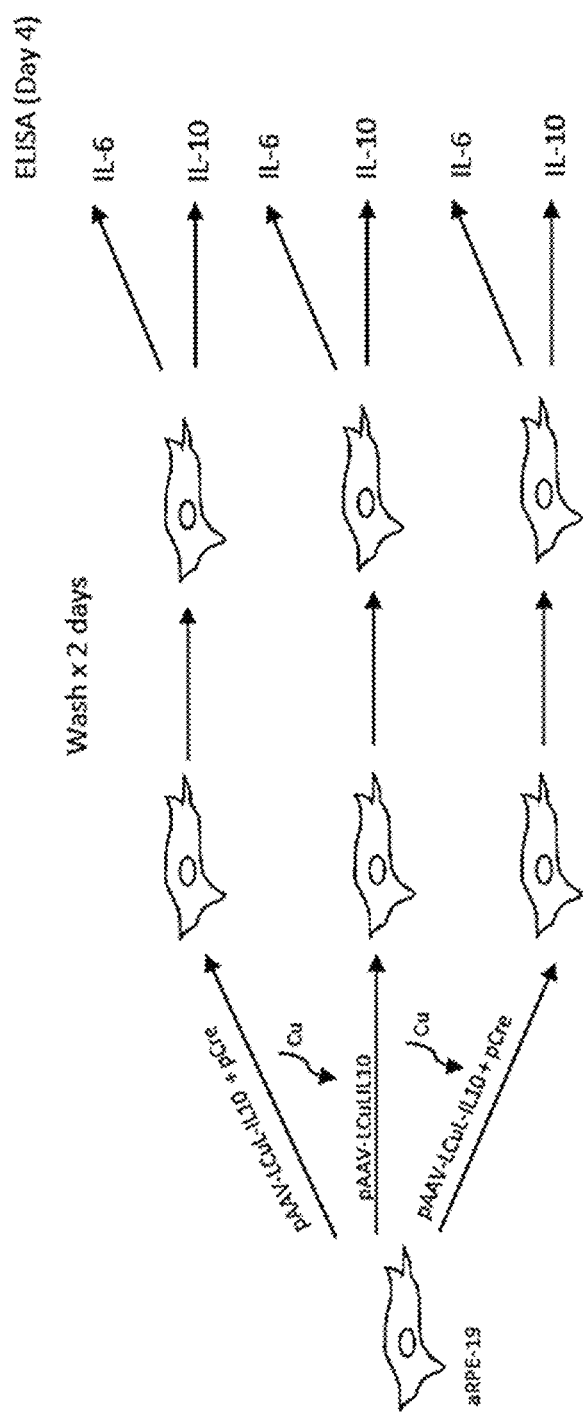

FIG. 11. Schematic of the experimental design used to evaluate a vector containing Cu regulated IL-10, flanked by LoxP sites, on the induction of proinflamatory signalling as determined by IL-6 expression with or without Cre. A human retinal pigmented epithelial cell line (aRPE-19) was transfected with vector constructs containing Cu regulatory sequences driving the expression of anti-inflammatory IL-10. The negative control consisted of the IL10 vector lacking Cu activation, treated with Cre. The IL-10 group consisted of the IL10 vector activated by Cu. The killed group consisted of activated IL10 vector, treated with Cre. Cells were assayed by ELISA for the expression of IL-10 and the pro-inflammatory marker IL-6.

Figure 12:
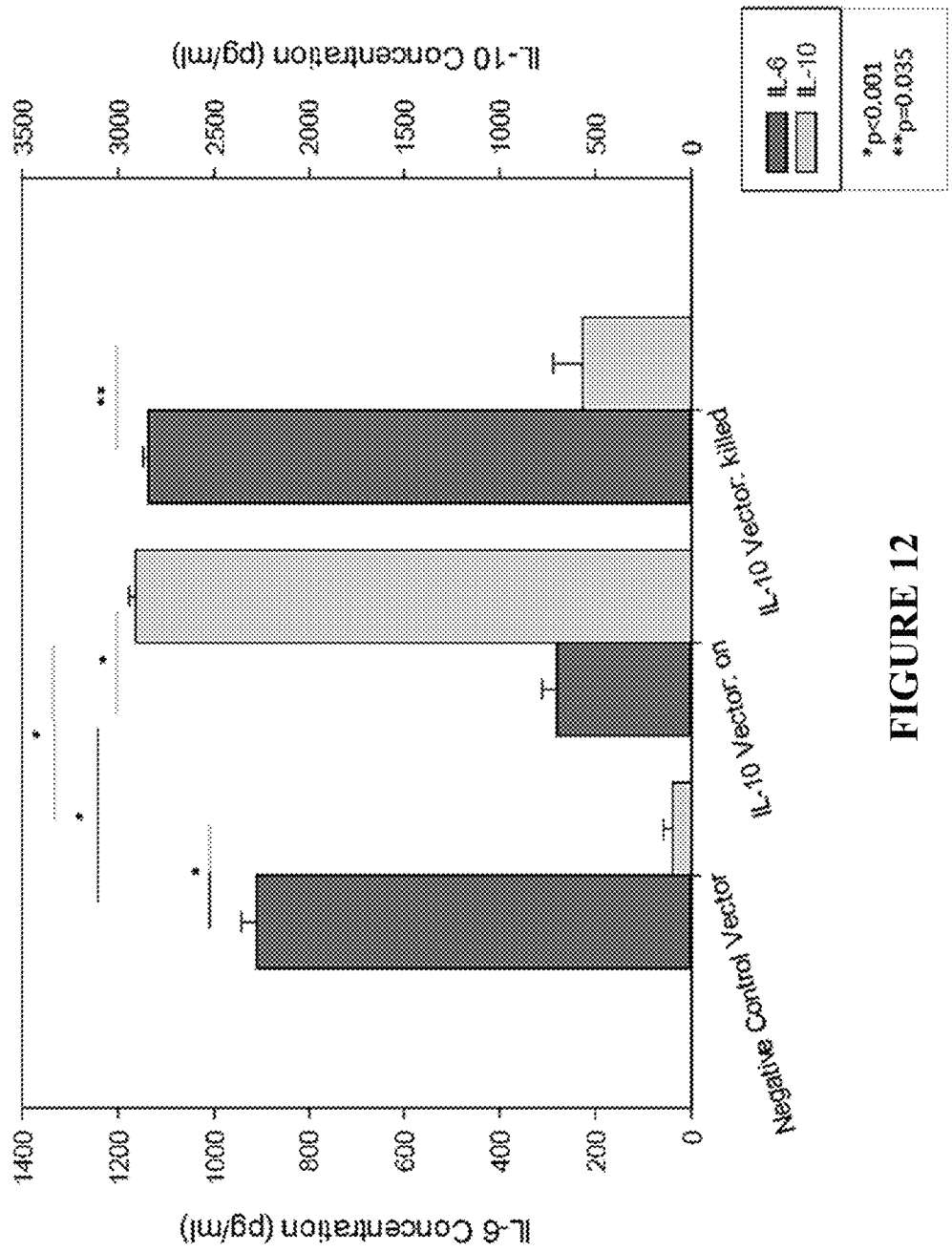

FIG. 12 Results obtained from simultaneous ELISAs of IL-10 and IL-6 following transfection with cumate regulated vectors containing IL-10 with or without the addition of Cre. In cells treated with the negative control vector (without Cu and with Cre), the level of IL-10 detected was low, correlating to high levels of the proinflamatory IL-6. Conversely, cells treated with the Cu regulated IL10 vector in the presence of Cu (IL10 vector: on) expressed high levels of IL-10 which correlated to low levels of IL-6 expression. Vectors where the IL-10 was excised by Cre (IL10 vector: killed) had IL-10 and IL-6 levels comparable to that of the negative control showing that the vector expression was successfully killed.

KEY TO SEQUENCE LISTING

SEQ ID NO: 1: Nucleic acid sequence, Kill switch vector backbone.
SEQ ID NO: 2: Nucleic acid sequence, reverse tetracycline-controlled transactivator (rtTA).
SEQ ID NO: 3: Nucleic acid sequence, Cumate Repressor (CymR).
SEQ ID NO: 4: Nucleic acid sequence, Tetracycline Promoter.
SEQ ID NO: 5: Nucleic acid sequence, Cumate Promoter.
SEQ ID NO: 6: Nucleic acid sequence, CMV-EF1-HTLV Promoter.
SEQ ID NO: 7: Nucleic acid sequence, Green fluorescent protein (GFP).
SEQ ID NO: 8: Nucleic acid sequence, Therapeutic polypeptide, Interleukin (IL)10.
SEQ ID NO: 9: Nucleic acid sequence, Therapeutic polypeptide, endo/angiostatin.
SEQ ID NO: 10: Nucleic acid sequence, Therapeutic polypeptide, Interleukin-1 Receptor Antagonist (IL-1RA).
SEQ ID NO: 11: Nucleic acid sequence, Therapeutic polypeptide, IL-10-IL-1RA.
SEQ ID NO: 12: Nucleic acid sequence, Nanoluciferase
SEQ ID NO: 13: Nucleic acid sequence, LoxP site
SEQ ID NO: 14: Nucleic acid sequence, Transcription blocker
SEQ ID NO: 15: Nucleic acid sequence, pAAV-LCuL-EAS
SEQ ID NO: 16: Nucleic acid sequence, pAAV-LCuL-IL10
SEQ ID NO: 17: Amino acid sequence, reverse tetracycline-controlled transactivator (rtTA)
SEQ ID NO: 18: Amino acid sequence, Cumate Repressor (CymR)
SEQ ID NO: 19: Amino acid sequence, Therapeutic polypeptide, Interleukin (IL)10
SEQ ID NO: 20: Amino acid sequence, Therapeutic polypeptide, endo/angiostatin
SEQ ID NO: 21: Amino acid sequence, Therapeutic polypeptide, Interleukin-1 Receptor Antagonist (IL-1RA)
SEQ ID NO: 22: Nucleic acid sequence, LoxP site—variant
SEQ ID NO: 23: Nucleic acid sequence, LoxP site—lox 511
SEQ ID NO: 24: Nucleic acid sequence, LoxP site—lox 5171
SEQ ID NO: 25: Nucleic acid sequence, LoxP site—lox 2272
SEQ ID NO: 26: Nucleic acid sequence, LoxP site—M2
SEQ ID NO: 27: Nucleic acid sequence, LoxP site—M3
SEQ ID NO: 28: Nucleic acid sequence, LoxP site—M7
SEQ ID NO: 29: Nucleic acid sequence, LoxP site—M11
SEQ ID NO: 30: Nucleic acid sequence, LoxP site—lox 71
SEQ ID NO: 31: Nucleic acid sequence, LoxP site—lox 66
SEQ ID NO: 32: Nucleic acid sequence, FRT site
SEQ ID NO: 33: Nucleic acid sequence, FRT site—variant
SEQ ID NO: 34: Nucleic acid sequence, FRT site—FL-IL-10A
SEQ ID NO: 35: Nucleic acid sequence, FRT site—FRT/FL-IL-10A
SEQ ID NO: 36: Nucleic acid sequence, rox site—WT
SEQ ID NO: 37: Nucleic acid sequence, rox site—rox7
SEQ ID NO: 38: Nucleic acid sequence, rox site—rox8
SEQ ID NO: 39: Nucleic acid sequence, rox site—rox12
SEQ ID NO: 40: Nucleic acid sequence, rox site—rox61
SEQ ID NO: 41: Nucleic acid sequence, rox site—rox85
SEQ ID NO: 42: Nucleic acid sequence, att site—attP
SEQ ID NO: 43: Nucleic acid sequence, att site—attB
SEQ ID NO: 44: Nucleic acid sequence, att site—proB
SEQ ID NO: 45: Nucleic acid sequence, att site—trpC
SEQ ID NO: 46: Nucleic acid sequence, att site—galT
SEQ ID NO: 47: Nucleic acid sequence, att site—thrA
SEQ ID NO: 48: Nucleic acid sequence, att site—rrnB

DETAILED DESCRIPTION OF THE INVENTION

Unless specifically defined otherwise, all technical and scientific terms used herein shall be taken to have the same meaning as commonly understood by one of ordinary skill in the art (e.g., molecular biology, gene therapy, genetic modification, biochemistry, physiology, and clinical studies).

Unless otherwise indicated, the molecular and statistical techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, TRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), J. E. Coligan et al. (editors) Current Protocols in Immunology, John Wiley & Sons (including all updates until present).

Various subjects can be administered an expression vector according to the present disclosure. In an example, the subject is a mammal. The mammal may be a companion animal such as a dog or cat, or a livestock animal such as a horse or cow. In another example, the subject is a human. Terms such as "subject", "patient" or "individual" are terms that can, in context, be used interchangeably in the present disclosure.

As used herein, terms such as "treating" or "treatment" refer to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease are mitigated or eliminated. In an example, the term "treatment" refers to both therapeutic treatment and prophylactic or preventative measures for ocular disorders such as, for example, exudative macular degeneration, diabetic retinopathy, cystoid macular oedema, clinically significant macular oedema, central retinal vein occlusion, branch retinal vein occlusion and ocular neovascularisation wherein the object is to reverse, prevent or slow down (lessen) the targeted disorder. Those in need of treatment include those already having an ocular disorder or those prone to having such disorders or those in whom such disorders are to be prevented. In an example, treatment encompasses stabilization and/or improvement of visual acuity.

An "effective amount" refers to at least an amount effective, at dosages and for periods of time necessary, to achieve the desired therapeutic or prophylactic result. An effective amount can be provided in one or more administrations. In some examples of the present disclosure, the term "effective amount" is used to refer to an amount necessary to effect treatment of an ocular disorder or condition as hereinbefore described. The effective amount may vary according to the disease or condition to be treated and also according to the weight, age, racial background, sex, health and/or physical condition and other factors relevant to the mammal being treated. Typically, the effective amount will fall within a relatively broad range (e.g. a "dosage" range) that can be determined through routine trial and experimentation by a medical practitioner. The effective amount can be administered in a single dose or in a dose repeated once or several times over a treatment period.

A "therapeutically effective amount" is at least the minimum concentration required to effect a measurable improvement of a particular ocular disorder (e.g. exudative macular degeneration). A therapeutically effective amount herein may also vary according to factors such as the disease state, age, sex, and weight of the patient, and the ability of the therapeutic to elicit a desired response in the individual. A therapeutically effective amount is also one in which any toxic or detrimental effects of the therapeutic are outweighed by the therapeutically beneficial effects. For exudative macular degeneration therapy, efficacy in vivo can, for example, be measured by one or more of the following: assessing the mean change in the best corrected visual acuity (BCVA) from baseline to a desired time, assessing the proportion of subjects who lose fewer than 15 letters in visual acuity at a desired time compared with baseline, assessing the proportion of subjects who gain greater than or equal to 15 letters in visual acuity at a desired time compared with baseline, assessing the proportion of subjects with a visual-acuity Snellen equivalent of 20/2000 or worse at a desired time, assessing the NEI Visual Functioning Questionnaire, assessing the size of choroidal neovascularization (CNV) and/or amount of leakage of CNV at a desired time, as assessed by fluorescein angiography.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers) that alter expression of a nucleic acid, e.g., in response to a developmental and/or external stimulus, or in a tissue specific manner.

Exemplary promoters can contain additional copies of one or more specific regulatory elements to further enhance expression and/or alter the spatial expression and/or temporal expression of said nucleic acid. In an example, the promoter is a regulatable promoter described herein. Other examples of promoters encompassed by the present disclosure include "constitutive promoters". Such promoters are constantly active (i.e. they constantly confer, activate or enhance the expression of a nucleic acid).

The term "operably linked" means positioning an expression element relative to a nucleic acid defined herein such that expression of the nucleic acid is controlled by the expression element.

As used in this specification and the appended claims, terms in the singular and the singular forms "a," "an" and "the," for example, optionally include plural referents unless the content clearly dictates otherwise. Thus, for example, reference to "a therapeutic moleucle" optionally includes one or more therapeutic molecules.

As used herein, the term "about", unless stated to the contrary, refers to +/−10%, more preferably +/−5%, more preferably +/−1%, of the designated value.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Kill Switch

Expression vectors encompassed by the present disclosure comprise a "kill switch". The term "kill switch" refers to element(s) of vectors defined herein that can silence expression of a nucleic acid encoding a therapeutic molecule(s) from the vector. The term "silence" is used in this context to refer to complete and irreversible suppression of expression. In an example, silencing completely abolishes expression of a nucleic acid encoding a therapeutic molecule from an expression vector defined herein.

In an example, the kill switch can facilitate removal of a nucleic acid sequence encoding a therapeutic molecule(s) or part thereof from the vector. In another example, the kill switch facilitates removal of some or all of the transcriptional machinery required for expression of the therapeutic molecule(s) from the vector. In another example, the kill switch facilitates removal of one or more promoters. In another example, the kill switch facilitates removal of a transactivator gene. In another example, the kill switch facilitates removal of the entire expression cassette from the vector (i.e. all foreign genes and regulatory elements are removed). In another example, the kill switch facilitates inversion of the sequence encoding one or more of the above elements. For example, the kill switch can facilitate inversion of some or all of the sequence(s) encoding a promoter(s), therapeutic molecule(s) or transactivator. An example of a kill switch vector backbone is provided in SEQ ID NO: 1.

In an example, the kill switch is a pair of site-specific recombination sequences. In this example, recombination between the site-specific recombination sequences silences expression of the nucleic acid encoding the therapeutic molecule. In another example, the kill switch is a pair of site-specific recombination sequences that are cleaved following contact with a recombinase. In an example, the site-specific recombination sequences "flank" the nucleic acid encoding the therapeutic molecule. Put another way, a first site-specific recombination sequence is positioned upstream of the therapeutic molecule and a second site-specific recombination sequence is positioned downstream of the therapeutic molecule. In another example, the site-specific recombination sequences flank some or all of the transcriptional machinery involved in expressing the nucleic acid encoding the therapeutic molecule. For example, the site-specific recombination sequences can flank one or more promoters disclosed herein. In another example, the site-specific recombination sequences flank all genes and regulatory elements in the vector. It will be appreciated by those skilled in the art that having site-specific recombination sequences that flank all genes and regulatory elements in the vector provides a safety mechanism, such that all foreign genes and regulatory elements can be removed from the vector in the case of, for example, an aberrant immune response or malignant transformation in the host.

One of skill in the art will appreciate that position and orientation of site-specific recombination sequences can direct inversion or excision of regions from vectors. Thus, in an example, site-specific recombination sequences are positioned to direct excision. For example, site-specific recombination sequences can be positioned in the same direction. In another example, site-specific recombination sequences can be positioned to direct inversion. For example, site-specific recombination sequences can be positioned in opposite orientations.

In an example, the kill switch can comprise a pair of LoxP sites which are cleaved following contact with Cre recombinase. Exemplary LoxP sites are described in Hoess et al. (1982) PNAS, 3398:402. For example, vectors defined herein can comprise canonical loxP sequences ATAACTTCGTATA-[spacer]-TATACGAAGTTAT. In an example, vectors defined herein can comprise a pair of sites having a nucleotide sequence shown in SEQ ID NO: 13. Other examples or LoxP sites are shown in Table 1.

TABLE 1

Examples of LoxP sites

| SEQ ID NO: | Name | 13bp Recognition Region | Spacer Region | 13bp Recognition Region |
|---|---|---|---|---|
| 22 | Variant | ATAACTTCGTATA | GCATACAT | TATACGAAGTTAT |
| 23 | lox 511 | ATAACTTCGTATA | ATGTATaC | TATACGAAGTTAT |
| 24 | lox 5171 | ATAACTTCGTATA | ATGTgTaC | TATACGAAGTTAT |
| 25 | lox 2272 | ATAACTTCGTATA | AaGTATcC | TATACGAAGTTAT |
| 26 | M2 | ATAACTTCGTATA | AgaaAcca | TATACGAAGTTAT |
| 27 | M3 | ATAACTTCGTATA | taaTACCA | TATACGAAGTTAT |
| 28 | M7 | ATAACTTCGTATA | AgaTAGAA | TATACGAAGTTAT |
| 29 | M11 | ATAACTTCGTATA | aGATAgaa | TATACGAAGTTAT |
| 30 | lox 71 | taccgTTCGTATA | NNNTANNN | TATACGAAGTTAT |
| 31 | lox 66 | ATAACTTCGTATA | NNNTANNN | TATACGAAcggta |

In another example, the kill switch can comprise a pair of short flippase recognition target (FRT) sites which are cleaved following contact with flippase (Flp). Exemplary FRT sites are described in Bolusani et al. 2006 Nucleic Acids Res. 34:5259-69. For example, vectors defined herein can comprise canonical FRT sequences GAAGTTCCTATTC-[spacer]-GtATAGGAACTTC (e.g., SEQ ID NO: 32). Other examples or FRT sites are shown in Table 2.

TABLE 2

Examples of FRT sites.

| SEQ ID NO: | Name | 13bp Recognition Region | Spacer Region | 13bp Recognition Region |
|---|---|---|---|---|
| 33 | Variant | GAAGTTCCTATAC | tttctaga | GAATAGGAACTTC |
| 34 | FL-IL-10A | agtGaTttgATAC | ttacatga | GtAaAGGAAtTag |
| 35 | FRT/FL-IL-10A | GAAGTTCCTATAC | ttacatga | GtAaAGGAAtTag |

In another example, the kill switch can comprise a pair of rox sites which are cleaved following contact with Dre recombinase. Exemplary rox sites are described in Anastassiadis et al., 2009 Dis Model Mech 2:508-515. For example, vectors defined herein can comprise a canonical rox sequence TAACTTTAAATAAT-[spacer]-ATTATT-TAAAGTTA. Other examples of rox sites are described in Chuang et al. 2016 G3 (Bethesda) 6:559-571, and include those shown in Table 3.

TABLE 3

Examples of rox sites.

| SEQ ID NO: | Name | 14bp Recognition Region | Spacer Region | 14bp Recognition Region |
|---|---|---|---|---|
| 36 | WT | TAACTTTAAATAAT | GCCA | ATTATTTAAAGTTA |
| 37 | rox7 | TAACTTTAAATAAg | GCCA | gTTATTTAAAGTTA |
| 38 | rox8 | TAACTTTAAATAAc | GCCt | CTTATTTAAAGTTA |
| 39 | rox12 | TAACTTTAAATAAg | GCCt | gTTATTTAAAGTTA |
| 40 | rox61 | TAACTTTAAATAAg | GCCc | gTTATTTAAAGTTA |
| 41 | rox85 | TAACTTTAAATAAg | GCCg | gTTATTTAAAGTTA |

In another example, the kill switch can comprise a pair of att sites which are cleaved following contact with phiC31 integrase. Exemplary att sites are described in Thorpe and Smith, 1998 PNAS 95:5505-5510. For example, vectors defined herein can comprise a canonical attP sequence TCAGCTTTTTTATACTAAGTTGG (SEQ ID NO: 42) and a canonical attB sequence CCTGCTTTTT-TATACTAACTTGA (SEQ ID NO: 43). Examples of secondary att sites include those shown in Table 4.

TABLE 4

Examples of secondary att sites.

| SEQ ID NO: | Name | Sequence |
|---|---|---|
| 44 | proB | TGCGCTAA TTTATAC GAGGCTAC |
| 45 | trpC | GCGTAATG TTTATAA ATGGCGGC |
| 46 | galT | CGCCTTTG TTTTCAA AAACCTGC |
| 47 | thrA | CGGGCTTT TTTCTGT GTTTCCTG |
| 48 | rrnB | TTGGCTAT TTTACCA CGACTGTC |

A kill switch defined herein can be activated using various mechanisms. For example, the kill switch can be contacted with a "kill switch activator". The term "kill switch activator" is used in the context of the present disclosure to refer to elements capable of activating a kill switch disclosed herein and silencing expression of a nucleic acid encoding a therapeutic polypeptide. In an example, the kill switch activator is an enzyme. For example, the enzyme can bind one or more of the above referenced site-specific recombination sequences. In an example, the enzyme is a recombinase. In an example, the enzyme is a tyrosine recombinase. In an example the enzyme is Cre recombinase (see for e.g. Sauer and Henderson (1988) PNAS 85:5166-5170; U.S. Pat. No. 4,959,317; accession P06956). In an example, the enzyme is Dre recombinase (see for e.g. Anastassiadis et al., 2009 Dis Model Mech 2:508-515; accession AAV84949). In another example, the enzyme is a flippase. For example, the enzyme can be FLP recombinase (see for e.g. Sadowski and Zhu (1995) J Biol Chem. 270:23044:23054; accession P03870). In another example, the enzyme is a serine recombinase. In an example the enzyme is phiC31 integrase (see for e.g. Thorpe and Smith, 1998 PNAS 95:5505-5510; accession NP_047974).

Expression Vector

The term "expression vector" is used in the context of the present disclosure to refer to a genetic construct which is capable of facilitating expression of a nucleic acid in a host cell. An expression vector can exist in the form of an isolated polynucleotide, for example "naked DNA", or can comprise one or more agents which enhance delivery to the host cell, such as a viral capsid and/or envelope, a lipid, or a polymer. Accordingly, examples of expression vectors encompassed by the present disclosure include, without limitation, naked DNA, phage, viruses, nanoparticles such as lipid-based nanoparticles, plasmids, linear DNA, cosmids, episomes, mini-circle DNA (for example, as described in US 2004/0214329), and bacteria. In another example, the expression vector is a transposon such as PiggyBac and PiggyBat (see Wu et al., PNAS, 103:15008-13, 2006; and WO 2010/085699).

Expression vectors encompassed by the present disclosure include DNA or RNA vectors. In an example, expression vectors are single stranded. In another example, expression vectors are double stranded.

Exemplary vector components include, but are not limited to, one or more of the following: a sequence encoding a therapeutic molecule and/or a regulator compound-binding polypeptide, a promoter such as a regulatable promoter defined herein, and a transcription termination sequence.

In an example, the expression vector is capable of transforming a host cell and effecting expression of a nucleic acid encoding a therapeutic molecule. In an example, the expression vector is also capable of replicating within the host cell. In another example, the expression vector is not capable of replicating within the host cell. In some examples, the expression vector is capable of integrating into the host cell's genome.

The selection of expression vector will depend on a variety of factors such as, for example, the host, immunogenicity of the vector, the desired duration of therapeutic molecule production, and the like. In one example, the expression vector is a viral vector. In one example, the expression vector is an adeno-associated virus (AAV) vector. In one example, the expression vector is a retroviral vector. In one example, the expression vector is a lentiviral vector. In one example, the expression vector is an adenovirus vector.

AAV vectors typically comprise inverted terminal repeats (ITRs) of 145 nt at either end, which contain sequences necessary for DNA replication and packaging into virions for nucleic acid delivery. In one example, the ITRs of AAV serotype 2 are used. However, ITRs from other suitable serotypes may be selected. These ITRs or other AAV components may be readily isolated using techniques available to those of skill in the art from an AAV serotype (see WO 2006/110689). Various recombinant AAV vector systems have been developed for nucleic acid delivery because they are non-pathogenic and exhibit a broad range of tissue specificity. AAV vectors can be readily constructed using techniques known in the art. See, e.g., U.S. Pat. Nos. 5,173,414 and 5,139,941; International Publication Nos. WO 1992/01070 and WO 1993/03769; Lebkowski et al. Molec. Cell. Biol. 5:3988-3996, 1988; Vincent et al. (1990) Vaccines 90 (Cold Spring Harbor Laboratory Press); Carter Current Opinion in Biotechnology 5:533-539, 1992; Muzyczka. Current Topics in Microbiol, and Immunol. 158:97-129, 1992; Kotin, Human Gene Therapy 5:793-801, 1994; Shelling and Smith Gene Therapy 7:165-169, 1994; and Zhou et al. J Exp. Med. 179:1867-1875, 1994.

In another example, the AAV is a self-complementary AAV (sc-AAV) (see for example, US2012/0141422). Self-complementary AAV vectors package an inverted repeat genome that can fold into dsDNA without the requirement for DNA synthesis or base-pairing between multiple vector genomes.

A retroviral vector generally comprises cis-acting long terminal repeats (LTRs) with packaging capacity for up to 6-10 kb of foreign sequence. The minimum cis-acting LTRs are sufficient for replication and packaging of a vector, which is then used to integrate an expression construct into the target cell to provide long term expression. Widely used retroviral vectors include those based upon murine leukemia virus (MuLV), gibbon ape leukemia virus (GaLV), simian immunodeficiency virus (SrV), human immunodeficiency virus (HIV), and combinations thereof (see, e.g., Buchscher et al., J Virol. 56:2731-2739 (1992); Johann et al, J. Virol. 65:1635-1640 (1992); Sommerfelt et al, Virol. 76:58-59 (1990); Wilson et al, J. Virol. 63:274-2318 (1989); Miller et al., J. Virol. 65:2220-2224 (1991); PCT/US94/05700; Miller and Rosman BioTechniques 7:980-990, 1989; Miller, A. D. Human Gene Therapy 7:5-14, 1990; Scarpa et al Virology 75:849-852, 1991; Burns et al. Proc. Natl. Acad. Sci USA 90:8033-8037, 1993).

Additional viral vectors include, for example, those derived from the pox family of viruses, such as vaccinia virus and avian poxvirus or an alphavirus or a conjugate virus vector (e.g. that described in Fisher-Hoch et al., PNAS 56:317-321, 1989).

In another example, the expression vector is a plasmid. In an example, the expression vector can be a high copy number plasmid. In an example, the high copy number plasmid can provide about 100-1,000 copies per cell. In another example, the high copy number plasmid can provide about 200-500 copies per cell. In another example, the expression vector is a low copy number plasmid. In an example, the low copy number plasmid can provide about 20-100 copies per cell. In another example, the low copy number plasmid can provide about 20-50 copies per cell.

Other suitable exemplary expression vectors also include those that function (i.e., direct expression) in mammalian, preferably human cells.

In some examples, the expression vector directs expression of the therapeutic polypeptide in a particular cell type. Thus, in some examples, the expression vector comprises a cell-type specific promoter. In one example, the expression vector comprises a retinal cell specific promoter, such as a mouse phosphoglycerate kinase 1 (PGK) promoter, elongation factor-1 (EFS) promoter, vitelliform macular dystrophy (VMD2) promoter, red/green opsin promoter, thymocyte antigen promoter or rhodopsin (Rho) promoter. In other examples, expression vectors direct expression in tumour cells. Such vectors can for example, comprise a tumour specific promoter(s) and/or a molecule that binds a tumour specific cell surface molecule to facilitate entry into tumour cells.

Expression vectors encompassed by the present disclosure may be modified to increase expression of nucleic acids encoding therapeutic molecules. Recombinant techniques useful for increasing expression include, but are not limited to, operatively linking nucleic acid sequences encoding therapeutic molecules to high-copy number plasmids, integration of the same molecule into one or more host cell chromosomes, addition of vector stability sequences, substitutions or modifications of transcription control signals (e.g., promoters, operators, enhancers), substitutions or modifications of translational control signals (e.g., ribosome binding sites, Shine-Dalgarno sequences), modification of nucleic acid sequences encoding a therapeutic molecule to correspond to the codon usage of the host cell, and the deletion of sequences that destabilise transcripts.

In some examples, expression vectors can contain regulatory sequences such as transcription control sequences, translation control sequences, origins of replication, and other regulatory sequences that are compatible with subjects and that control the expression of nucleic acid sequences encoding therapeutic molecules. Transcription control sequences are sequences which control the initiation, elongation, and/or termination of transcription. Particularly important transcription control sequences are those which control transcription initiation, such as promoter, enhancer, operator and repressor sequences. A variety of suitable transcription control sequences are known to those skilled in the art. Examples include tac, lac, trp, trc, oxy-pro, omp/lpp, rrnB, bacteriophage lambda, bacteriophage T7, T71ac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences.

In an example, the expression vector further comprises a transcription blocker between a constitutive and a regulatable promoter. Transcription blockers can be used in order to prevent transcriptional interference between multiple promoters in close proximity. Such transcription blockers are advantageous for tightly regulated expression systems such as those utilised for gene therapy. Transcription blockers can comprise one or more polyadenylation signal sequences and transcription pause sites for reducing background expression. Suitable transcription blockers are described in, for example, Eggermont and Proudfoot, EMBO J, 12:2539-2548, 1993. In one example, the transcription blocker comprises a sequence set forth in SEQ ID NO: 14.

In another example, the expression vector comprises the nucleic acid sequence shown in SEQ ID NO: 15. In another example, the expression vector comprises the nucleic acid sequence shown in SEQ ID NO: 16.

Regulatable Elements, Regulator Compounds and Regulator Compound-Binding Molecules In an example, vectors defined herein comprise a regulatable element operably linked to a nucleic acid sequence encoding a therapeutic molecule. For example, the regulatable element can be operably linked to a nucleic acid sequence encoding a therapeutic molecule described below.

The term "regulatable element" is used in the context of the present disclosure to refer to a recombinant, synthetic or fusion nucleic acid(s) which confers, activates, enhances or represses the expression of a nucleic acid to which it is operably linked. For example, a regulatable element operably linked to a therapeutic molecule defined herein confers, activates, enhances or represses expression a therapeutic molecule defined herein.

In an example, the regulatable element can comprise a nucleic acid sequence which is responsive to the presence of a regulator compound. In an example, the regulatable element can respond to the presence of a regulator compound by promoting expression of an operably linked nucleic acid. In another example, the regulatable element can respond to the presence of a regulator compound by repressing expression of an operably linked nucleic acid.

The regulatable element is not particularly limited so long as it can selectively regulate expression of a therapeutic molecule from a vector defined herein. In an example, the regulatable element comprises one or more of a tetracycline responsive element (TRE), a cumate operator (CuO), an ecdysone response element (EcRE), a hormone response element (HRE), an estrogen response element (ERE), a glucocorticoid response element (GRE), a progesterone response element (PRE), a heat shock sequence element (HSE).

In an example, the regulatable element is a regulatable promoter. Examples of regulatable promoters include, without limitation, tetracycline-regulated promoters (e.g. SEQ ID NO: 4), cumate-regulated promoters (e.g. SEQ ID NO: 5), rapamycin-inducible promoters, steroid hormone-inducible promoters, metal-responsive promoters, heat shock response promoters, light-responsive promoters, interferon-responsive promoters, and mifepristone-regulated promoters. Examples of regulatable promoters are described in Goverdhana et al., Mol Ther, 12:189-211, 2005; Agha-Mohammadi and Lotze, J Clin Invest, 105:1177-1183; and Mullick et al., BMC Biotech, 6:43, 2006). Other examples of regulatable promoters include hypoxia driven promoters, which are active when ocular neovascularization or age-related macular degeneration is associated with hypoxia, IL-8 promoters, or metallothionine-inducible promoters.

In one example, the regulatable promoter is a tetracycline-regulated promoter. In another example, the regulatable promoter is a cumate-regulated promoter.

In an example, the regulatable promoter comprises a sequence set forth in SEQ ID NO: 4 or SEQ ID NO: 5. In an example, the nucleic acid sequence of the regulatable promoter consists of a sequence set forth in SEQ ID NO: 4 or SEQ ID NO: 5.

The activity (i.e. ability to confer, activate, enhance or repress the expression of a nucleic acid) of "regulatable elements" such as regulatable promoters encompassed by the present disclosure is regulated by regulator compound either alone or in conjunction with a regulator compound-binding protein.

In an example, a regulator compound can directly bind the regulatable promoter to regulate its activity. For example, binding of the regulator compound to the regulatable promoter can promote expression of the nucleic acid encoding the therapeutic polypeptide. In another example, binding of the regulator compound to the regulatable promoter represses expression of the nucleic acid encoding the therapeutic molecule.

In another example, a regulator compound must bind a regulator compound binding molecule expressed from an expression vector defined herein in order to bind and regulate activity of the regulatable promoter. In an example, the regulator compound binding molecule is operably linked to a constitutive promoter in an expression vector defined herein. In this example, the regulator compound-binding molecule is continuously expressed from an expression vector defined herein and, upon contact with a regulator compound is capable of binding and regulating activity of the regulatable promoter operably linked to the therapeutic polypeptide.

Various constitutive promoters that may be operably linked to a nucleic acid encoding a regulator compound-binding molecule are known in the art. Examples include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. For example, the constitutive promoter can be a composite human CMV-EF1-HTLV promoter.

In an example, the constitutive promoter comprises a sequence set forth in SEQ ID NO: 6. In an example, the nucleic acid sequence of the constitutive promoter consists of a sequence set forth in SEQ ID NO: 6.

In an example, the regulator compound-binding molecule and the therapeutic molecule are expressed from the same vector. In another example, the regulator compound-binding molecule and the therapeutic molecule are expressed from separate vectors.

One of skill in the art will appreciate the appropriate regulator compound will be dictated by the regulatable promoter and/or the regulator compound-binding molecule. For example, an appropriate regulator compound for a tetracycline regulatable promoter would be tetracycline or a structural analogue thereof such as doxycycline. In another example, an appropriate regulator compound for a cumate regulatable promoter would be cumate or a structural analogue thereof. In another example, an appropriate regulator compound for a rapamycin-inducible promoter would be rapamycin or a structural analogue thereof. In another example, an appropriate regulator compound for a steroid hormone-inducible promoter would be a steroid hormone such as progesterone or a structural analogue thereof such as mifepristone.

In an example, the regulator compound is a small molecule. In one example, the regulator compound is tetracycline. In one example, the regulator compound is cumate. In one example, the regulator compound is rapamycin.

In some examples, the regulator compound is a steroid hormone, or an analogue thereof. In one example, the regulator compound is progesterone. In one example, the regulator compound is ecdysone. In one example, the regulator compound is glucocorticoid. In one example, the regulator compound is estrogen. In one example, the regulator compound is mifepristone.

In one example, the regulatable element comprises a tetracycline responsive element (TRE) and the regulator compound is tetracycline or a structural analogue thereof. In one example, the regulatable element comprises a cumate operator (CuO) and the regulator compound is cumate or a structural analogue thereof. In one example, the regulatable element comprises an ecdysone response element (EcRE) and the regulator compound is ecdysone or a structural analogue thereof. In one example, the regulatable element comprises an estrogen response element (ERE) and the regulator compound is estrogen or a structural analogue thereof. In one example, the regulatable element comprises a glucocorticoid response element (GRE) and the regulator compound is a glucocorticoid or a structural analogue thereof. In one example, the regulatable element comprises a progesterone response element (PRE) and the regulator compound is progesterone or a structural analogue thereof.

Again, one of skill in the art will appreciate the appropriate combinations of regulator compound and regulator compound-binding molecule. In an example, the regulator compound-binding molecule is a polypeptide. In an example, the regulator compound-binding molecule comprises a tetracycline-controlled transactivator (tTA), tetracycline repressor (TetR), or reverse tetracycline-controlled transactivator (rtTA) (e.g. SEQ ID NO: 2; SEQ ID NO: 17). In another example, the regulator compound-binding molecule comprises a cysteine metabolism repressor (CymR) (e.g. SEQ ID NO: 3; SEQ ID NO: 18). In another example, the regulator compound-binding molecule comprises a steroid hormone receptor, such as a progesterone receptor, an estrogen receptor (ER) or an ecdysone receptor (EcR). In some examples the regulator compound-binding molecule comprises a rapamycin binding protein. In some examples the regulator compound-binding molecule comprises a Gal4 DNA binding domain. In some examples the regulator compound-binding molecule comprises a VP16 activation domain. In another example, the regulator compound-binding molecule is a fusion of one or more of the molecules described herein. For example, the regulator compound-binding molecule can comprise a fusion of CymR and a VP16 activation domain.

In an example, the regulator compound-binding molecule comprises an amino acid sequence set forth in SEQ ID NO: 17 or SEQ ID NO: 18. In an example, the regulator compound-binding molecule consists of an amino acid sequence set forth in SEQ ID NO: 17 or SEQ ID NO: 18.

Therapeutic Molecule

Therapeutic molecules encompassed by the present disclosure are not particularly limited so long as they can be expressed from an expression vector disclosed herein or translated from a nucleic acid sequence expressed from the same.

In an example, the expressed nucleic acid sequence encodes a therapeutic polypeptide. For example, a nucleic acid sequence can be expressed from an expression vector defined herein and translated by cellular machinery to produce a therapeutic polypeptide.

Exemplary therapeutic polypeptides include binding proteins such as immunoglobulin, antibodies and antigenic binding fragments. For example, therapeutic polypeptides include single chain Fv fragment (scFv), dimeric scFv (di-scFv), (scFv)$_n$, scFv or di-scFv linked to a constant region of an antibody, Fc or a heavy chain constant domain (CH)2 and/or CH3, diabodies, triabodies, tetrabodies, Fab, F(ab')$_2$ and antibodies. In an example, the therapeutic polypeptide is an antibody or TRAP molecule. Examples of such therapeutic molecules include ranibizumab, bevacizumab and aflibercept.

In another example, the therapeutic polypeptide comprises an antigen binding site of an antibody.

In another example, the therapeutic molecule can be an inhibitory oligonucleotide. Exemplary inhibitory oligonucleotides include isolated or synthetic antisense RNA or DNA, siRNA or siDNA, miRNA, miRNA mimics, shRNA or DNA and Chimeric Antisense DNA or RNA. The term "antisense" as used herein means a sequence of nucleotides complementary to and therefore capable of binding to a coding sequence, which may be either that of the strand of a DNA double helix that undergoes transcription, or that of a messenger RNA molecule. The terms "short hairpin RNA" or "shRNA" refer to an RNA structure having a duplex region and a loop region. The term small interfering RNA (siRNA), sometimes known as short interfering RNA or silencing RNA, is a class of double-stranded RNA molecules, 20-25 base pairs in length. A siRNA that inhibits or prevents translation to a particular protein is indicated by the protein name coupled with the term siRNA. Thus a siRNA that interferes with the translation of VEGF is indicated by the expression "VEGF siRNA". The term "microRNA" (abbreviated miRNA) is a small non-coding RNA molecule (containing about 22 nucleotides) found in plants, animals and some viruses, that functions in RNA silencing and post-transcriptional regulation of gene expression. The prefix "miR" is followed by a dash and a number, the latter often indicating order of naming. Different miRNAs with nearly identical sequences except for one or two nucleotides are annotated with an additional lower case letter. Numerous miRNAs are known in the art (miRBase V.21 nomenclature; Kozomara et al. 2013; Griffiths-Jones, S. 2004). In another example, an inhibitory oligonucleotide encompassed by the present disclosure inhibits the activity of one or more miRNAs. Various species are suitable for this purpose. Examples include antagomirs, interfering RNA, ribozymes, miRNA sponges and miR-masks. The term "antagomir" is used in the context of the present disclosure to refer to chemically modified antisense oligonucleotides that bind to a target miRNA and inhibit miRNA function by preventing binding of the miRNA to its cognate gene target.

In an example, the therapeutic molecule is an "anti-angiogenic molecule". The term "anti-angiogenic molecule" is used in the context of the present disclosure to refer to molecules expressed from an expression vector defined herein which inhibit the development of blood vessels, e.g., inhibit angiogenesis, endothelial cell growth, stability of blood vessels, and/or vasculogenesis. Anti-angiogenic molecules encompassed by the present disclosure include polynucleotide(s), polypeptide(s), antibod(ies) or conjugates or fusion proteins thereof. Exemplary anti-angiogenic molecules include inhibitors of VEGF and members of the VEGF family, P1GF, PDGF family, fibroblast growth factor family (FGFs), TIE ligands (Angiopoietins), ephrins, ANGPTL3 and ANGPTL4. In other examples, anti-angiogenic molecules inhibit growth hormones such as insulin-like growth factor-I (IGF-I), VIGF, epidermal growth factor (EGF), CTGF and members of the CTGF family, TGF-α and TGF-β. Other examples of anti-angiogenic molecules include antibodies to VEGF, antibodies to VEGF receptors and angiogenesis inhibitors such as angiostatin, endostatin and fusions thereof. Accordingly, in an example, the therapeutic molecule comprises endostatin and/or angiostatin (e.g. SEQ ID NO: 9; SEQ ID NO: 20). In another example, the therapeutic molecule is a fusion of one or more of the molecules described herein. For example, the therapeutic molecule can comprise a fusion of endostatin and angiostatin.

In an example, the therapeutic molecule is an anti-inflammatory molecule. In an example, the anti-inflammatory molecule is an interleukin such as IL-10, IL-4, IL-6, IL-11 or IL-13. For example, the anti-inflammatory molecule can be IL-10 (e.g. SEQ ID NO: 8; SEQ ID NO: 19). In another example, the anti-inflammatory molecule is interleukin IL-1 receptor antagonist (IL-1RA) (e.g. SEQ ID NO: 10; SEQ ID NO: 21), or a fusion of IL-10 and IL-1RA (e.g. SEQ ID NO: 11). In other examples, the anti-inflammatory molecule inhibits a pro-inflammatory cytokine such as IL-1, tumour necrosis factor alpha (TNF-α) or IL-18. In other examples, anti-inflammatory molecules increase the production or number of CD14+CD16+ cells in a subject, reduce IL-6 levels, reduce TNF-alpha levels and/or increase IL-10 levels.

In another example, the therapeutic molecule is a neurotrophic factor. Neurotrophic factors are thought to be responsible for the maturation of developing neurons and for maintaining adult neurons. In this regard, neurotrophic factors can be used to inhibit or reverse neural cell degeneration and death. Examples of neurotrophic factors include, for example, brain-derived neurotrophic factor, nerve growth factor, transforming growth factors, glial cell-line derived neurotrophic factor, neurotrophin 3, neurotrophin 4/5, and interleukin 1-B.

In another example, the therapeutic molecule is cytotoxic to cancer cells. In other examples, the therapeutic molecule inhibits one or more of Nuclear factor-kappa B (NFκB), C-kit (CD117, stem cell-factor receptor), Heat shock protein 90 (Hsp90), Ras-Raf mitogen-activated protein kinase (IEK) pathway, Bcl-2, IL-2.

In an example, the therapeutic molecule comprises an amino acid sequence set forth in SEQ ID NOs: 19 to 21. In an example, the regulator compound-binding molecule consists of an amino acid sequence set forth in SEQ ID NOs: 19 to 21.

Treatment and Prevention

The methods of the present disclosure are directed towards the treatment and/or prevention of an ocular disorder. The term "ocular disorder" is used in the context of the present disclosure to refer to disorders and anomalies that affect the human eye and visual system. For example, ocular disorders include, but are not limited congenital, developmental, inflammatory, infectious, vascular, occlusive, angiogenic, degenerative, neoplastic, pre-neoplastic, iatrogenic, traumatic, glaucomatous, post-transplant complications, cataractous, and idiopathic diseases of the eye, retina, choroid or macula, or the systemic predispositions, associations or complications of these diseases (such as metastatic uveal melanoma or multisystem effects in an inherited gene dystrophy).

Other exemplary ocular disorders include diabetic retinopathy, cystoid macular oedema, clinically significant macular oedema, uveitis, iritis, giant cell arteritis, vasculitis, pars planitis, corneal transplant rejection, intraocular inflammation and lamellar corneal transplant rejection. Other examples of ocular disorders encompassed by the present disclosure include macular degeneration, diabetic retinopathy, cystoid macular oedema, clinically significant macular oedema, central retinal vein occlusion, branch retinal vein occlusion or ocular neovascularisation. For example, the ocular disorder can be an "intraocular neovascular disease". The term, "intraocular neovascular disease" is used in the context of the present disclosure to refer to a disease characterized by ocular neovascularization. Examples of intraocular neovascular diseases include, but are not limited to, e.g., proliferative retinopathies, choroidal neovascularization (CNV), dry age-related macular degeneration (AMD), wet age-related macular degeneration (AMD), diabetic and other ischemia-related retinopathies, diabetic macular edema, pathological myopia, von Hippel-Lindau disease, histoplasmosis of the eye, Central Retinal Vein Occlusion (CRVO), corneal neovascularization and retinal neovascularization. For example, the methods of the present disclosure encompass treating wet AMD. In another example, the methods of the present disclosure encompass treating CNV.

In an example, the methods of the present disclosure encompass inhibition of endothelial cell growth in the retina. For example, the methods of the present disclosure encompass inhibition of endothelial cell growth in the sub-retinal pigment epithelium and/or sub retinal space.

In another example, the ocular disorder is an infection.

In another example, the ocular disorder is a cancer. In one example, the cancer is uveal melanoma, ciliary body melanoma, iris melanoma, choroidal melanoma, intraocular lymphoma, retinoblastoma, or medulloepithelioma, choroidal hemangioma, choroidal metastasis, conjunctival Kaposi's sarcoma, malignant conjunctival tumor, orbital or lacrimal gland lymphoma, lymphoma of the conjunctiva, conjunctival melanoma or primary acquired melanosis with atypia, malignant tumour of the orbit, malignant tumour of the lacrimal gland, pigmented conjunctival tumour, squamous carcinoma of the conjunctiva, intraepithelial neoplasia of the conjunctiva or ocular surface squamous neoplasia. In one example, the cancer is uveal melanoma.

In another example, the ocular disorder is choroidal nevus, choroidal osteoma, nevus of Ota, conjunctival naevus, epibulbar dermoid, benign tumors of the lacrimal gland, benign tumours of the orbit, manifestations of thyroid ophthalmopathy, pingueculum, or pterygium.

In another example, the ocular disorder is Leber congenital amaurosis with RPE65 or an ocular disorder caused by RPE65 mutations. In another example, the ocular disorder is retinitis pigmentosa caused by a mutation in MERTK or RPGR or PDE6B or RLBP1 or other genes, or another disease caused by a mutation in MERTK or RPGR or PDE6B or RLBP1. In another example, the ocular disorder is choroideraemia or an ocular disorder caused by mutations in CHM. In another example, the ocular disorderis Achromatopsia or an ocular disorder caused by mutations in the CNGA3, CNGB3, GNAT2, PDE6C, PDE6H and ATF6 genes. In another example, it is X-linked retinoschisis or an ocular disorder caused by mutations in RS1. In another example, the ocular disorder is Leber's Hereditary Optic Neuropathy. In another example, the ocular disorder is a complication of transplant.

In an example, the above referenced methods comprise administering an expression vector described herein. For example, the above referenced methods can comprise administering an expression vector which comprises a kill switch and a nucleic acid encoding a therapeutic molecule, wherein activation of the kill switch silences expression of the nucleic acid encoding the therapeutic molecule. In an example, the vector further comprises a regulatable element operably linked to the nucleic acid encoding the therapeutic molecule, wherein activity of the regulatable promoter is regulated by administration of a regulator compound to the subject. In an example, the expression vector further comprises a constitutive promoter operably linked to a regulator compound-binding molecule which binds the regulator compound, wherein upon binding the regulator compound, the regulator binding-polypeptide regulates expression of the therapeutic molecule.

In another example, the regulator compound-binding molecule and therapeutic molecule are expressed from separate expression vectors.

Formulations

Expression vectors, regulator compounds and other molecules described herein may be formulated as a pharmaceutical composition suitable for administration to a subject. Exemplary pharmaceutical compositions can comprise a pharmaceutically acceptable carrier, diluent or excipient. Depending upon the particular route of administration, a variety of acceptable carriers, known in the art may be used, as for example described in Remington's Pharmaceutical Sciences (Mack Publishing Co. N.J. USA, 1991).

Exemplary pharmaceutical compositions may also comprise pharmaceutically acceptable sterile aqueous or non-aqueous solutions, dispersions, suspensions, or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils, and injectable organic esters such as ethyl oleate. Compositions may also contain adjuvants such as preservatives, wetting agents, emulsifying agents, and dispersing agents or antibacterial and antifungal agents.

In another example, expression vectors can be incorporated into slow release or targeted delivery systems. Exemplary slow release systems include polymer matrices, liposomes, and microspheres. Liposomes may be biodegradable and amphiphilic drug delivery systems, which may be formulated using phospholipids and cholesterol. Microspheres may be formulated using biodegradable and biocompatible polymers.

In an example, regulator compounds are provided in a topical formulation. For example, regulator compounds can be provided as an eye drop formulation. Suitable exemplary eye drop formulations include solutions, suspensions, ointments, gels or foams. In an example, the eye drop formulation comprises a regulator compound defined herein and a suitable carrier. Exemplary carriers include saline solution, water polyethers such as polyethylene glycol, polyvinyls such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate and salts such as sodium chloride and potassium chloride.

In an example the expression vector is present in or on a device that allows controlled or sustained release of the expression vector, such as an ocular sponge, meshwork, mechanical reservoir, or mechanical implant. Implants (see, e.g., U.S. Pat. Nos. 5,443,505, 4,853,224 and 4,997,652), devices (see, e.g., U.S. Pat. Nos. 5,554,187, 4,863,457, 5,098,443 and 5,725,493), such as an implantable device, e.g., a mechanical reservoir, an intraocular device or an extraocular device with an intraocular conduit, or an implant or a device comprised of a polymeric composition are particularly useful for ocular administration of the expression vector.

In an example, the expression vector is formulated to enhance transduction efficiency, i.e., to enhance transduction of the vector into a host cell. Suitable compositions are further described in U.S. Pat. Nos. 6,225,289 and 6,514,943.

Administration and Dosing

In an example, an expression vector defined herein is administered to a subject. Expression of a therapeutic molecule from the expression vector is subsequently regulated via administration of a regulator compound to the subject. Expression of the therapeutic molecule is subsequently silenced by administering a kill switch activator to the subject or by administering a vector comprising a nucleic acid sequence encoding a kill switch activator. Each of the vector, regulator compound and kill switch activator can be administered to a subject as a pharmaceutical composition. The selection of administration route will depend on a variety of factors such as, for example, the host, immunogenicity of the vector, the desired duration of therapeutic molecule production, and the like.

The pharmaceutical composition can, for example, be administered topically. For example, the composition can be administered by way of eye drops. In this example, the composition or part thereof can diffuse into the intraocular environment through the hydrophobic cornea. In another example, the composition is administered via intravitreal injection. In another example, the composition is administered via subretinal injection. In one example, a vitrectomy is performed prior to subretinal injection. In another example, the composition is administered via subcutaneous injection. In another example, the composition is administered via intramuscular injection. In another example, the composition is administered via intravenous injection. In another example, the composition is administered as a food or drink composition. In other examples involving use of heat or light as regulator compounds, such compounds can be applied to the eye of a subject as required.

In an example a pharmaceutical composition comprising a vector is administered via an ophthalmologic instrument for delivery to a specific region of an eye. Use of a specialized ophthalmologic instrument ensures precise administration of the expression vector while minimizing damage to adjacent ocular tissue. Delivery of the expression vector to a specific region of the eye also limits exposure of unaffected cells to the therapeutic molecule, thereby reducing the risk of side effects. One example of such an ophthalmologic instrument is a combination of forceps and subretinal needle or sharp bent cannula.

In one example, a pharmaceutical composition comprising an expression vector is administered by intravitreal or subretinal injection, a pharmaceutical composition comprising a regulator compound(s) is subsequently administered topically by way of eye drops and a kill switch activator is subsequently administered topically and/or by intravitreal or subretinal injection.

In another example, a pharmaceutical composition comprising an expression vector is administered by intravitreal or subretinal injection, a food or drink composition comprising a regulator compound(s) is subsequently administered and a kill switch activator is subsequently administered topically and/or by intravitreal or subretinal injection.

In an example, a kill switch activator can be expressed from a vector described herein. In an example, two vectors can be administered to a subject, the first comprising the kill switch and the second comprising a nucleic acid sequence encoding a kill switch activator. Thus, the first vector can be administered to express the therapeutic molecule and then subsequently, when expression of the therapeutic molecule is no longer required or desired, the second vector can be administered to express the kill switch activator thereby silencing expression of the therapeutic molecule. In some examples, the nucleic acid sequence encoding the kill switch activator is operably linked to a regulatable promoter.

In another example, vectors comprising a kill switch disclosed herein can further comprise a kill switch activator operably linked to a regulatable promoter. Thus, in some examples, nucleic acid sequences encoding both the therapeutic molecule and the kill switch activator can be present in the same vector. In this example, a regulator compound is administered to the subject to activate the regulatable promoter, promote expression of the kill switch activator and thus activate the kill switch to silence expression of therapeutic molecule(s) from the vector. Likewise, in another example, a regulator compound-binding molecule can be expressed from another vector. For example, two vectors can be administered to a subject, the first comprising the regulatable element and the second comprising a constitutive promoter operably linked to a nucleic acid encoding a regulator compound-binding molecule. In this example, a regulator compound is administered to the subject to bind the regulator compound-binding molecule and regulate expression of the regulatable promoter.

One of skill in the art will appreciate that dosage and routes of administration can be selected to minimize loss of expression vector due to a host's immune system. For example, for contacting ocular cells in vivo, it can be advantageous to administer to a host a null expression vector (i.e., an expression vector not comprising the nucleic acid sequence encoding the therapeutic molecule) prior to performing the methods described herein. Prior administration of null expression vectors can serve to create an immunity (e.g., tolerance) in the host to the expression vector, thereby decreasing the amount of vector cleared by the host's immune system.

Compositions disclosed herein can also be administered systemically, such as, for example, by intravenous or intraperitoneal administration. In another example, compositions can be administered orally. In another example, compositions can be administered intranasally.

In an example a first dose is administered to a subject followed by one or more subsequent doses. In an example, the first dose comprises a vector disclosed herein. In one example, one or more subsequent doses comprising the vector are administered. A regulator compound may be administered simultaneously or as one or more subsequent doses to regulate expression of a therapeutic molecule from the vector. For example, a first dose comprising a vector disclosed herein can be administered to a subject and a series of subsequent doses comprising a regulator compound can be administered to the subject. In this example, at least two, three, four, five, six, seven, eight, nine, ten, 15, 20, 30, 50, 100 or more subsequent doses can be administered to the subject. In this example, the subsequent dose of regulator compound can be provided simultaneously or sequentially with a subsequent dose of an expression vector disclosed herein. In an example, dosing is daily, every other day, every other week, every other month. In an example, a daily dose comprises a single application or multiple applications per administration. For example, at least two, three, four or more applications can be provided per day of administration.

Kits

Compositions according to the present disclosure can be provided in a kit or pack. For example, compositions disclosed herein may be packaged in a suitable container with written instructions for treating an ocular disorder. In an example, compositions may be provided in single dose containers such as an eye dropper or pre-filled syringe.

Kits of the present disclosure may comprise a therapeutic system. Such therapeutic systems can provide pre-programmed, unattended delivery of a composition at a rate, and for a time period, established to meet a specific therapeutic need. The system can be designed to minimize the patient's intervention and to optimize compliance with the prescribed regimen, for example.

In one example, the kit comprises an expression vector(s) defined herein and an eye drop formulation comprising a regulator compound(s) defined herein for use in methods of treating an ocular disorder.

In one example, the kit further comprises a kill switch activator as defined herein.

In one example, the kit further comprises an expression vector comprising a nucleic acid sequence encoding a kill switch activator as defined herein.

In one example, the kit comprises an expression vector(s) defined herein, an eye drop formulation comprising tetracycline, and Cre recombinase or an expression vector comprising a nucleic acid sequence encoding a Cre recombinase.

EXAMPLES

Example 1—Methods

Construction of Vectors

The pAAV.LL Kill switch vector backbone (FIG. 1) was synthetically constructed and ligated into pAAV-mcs containing AAV ITRs. Each of the vector inserts were also synthetically synthesized with restriction sites to allow cloning into the pAAV.LL backbone. The tetracycline or cumate repressor genes, flanked by XbaI and EcoRI sites were cloned into the XbaI-EcoRI site on the backbone. The tetracycline or cumate responsive promoters and CMV promoter flanked by BstBI and SalI sites were cloned into the unique BstBI-SalI site in the backbone. Finally, the gene of interest (GFP, IL-10, Endo/angiostatin, IL-1RA and IL-10-IL-1RA) flanked by SalI and NheI was cloned into the SalI-NheI site. Nano-luciferase was cloned into the SalI-Nhe site on the kill switch vector with the compatible XhoI and XbaI sites (FIG. 2).

Evaluating the Effects of the Kill Switch in Vector Constructs Containing the Marker Gene, Luciferase ARPE-19 cells were cultured in T-75 tissue culture flasks with DMEM/F12 media supplemented with 10% Fetal Calf Serum (FCS) and 100 I.U/ml penicillin/streptomycin (P/S) until about 80% confluence. Cells were trypsinized with 0.05% Trypsin-EDTA and seeded at a concentration of 20,000 cells/well in a 96-well tissue culture treated plate. After 12-24 hours, cells were transfected using lipofectamine 3000 (Life technologies; MA, USA) with pAAV-LTetL-luc, pAAV-LCuL-luc and pAAV-LCMVL-luc all containing the marker gene, nano-luciferase.

24 hours post transfection, the cells were washed gently and media replaced with a subset of cells activated with doxycycline (structural tetracycline analogue) and cumate and a corresponding subset of cells with no activation (FIG. 4). On day 4, luminescence was measured using the Nano-Glo Luciferase assay (Promega; WI, USA) to ensure activation, following which, a subset of activated cells were transfected with a vector containing Cre. The cells were washed daily and luminescence was measured on day 7. Briefly, the Nano-Glo Luciferase Assay was performed by adding 10 ul of media from each treatment well to a black, clear bottom, 384 well plate. 10 ul of the promega substrate was subsequently added to these wells, mixed and left for 3 minutes at room temperature. Luminescence was read on a Luminescence plate reader. The schematic for this experiment is shown in FIG. 4 and the results of vector killing is shown in FIG. 5.

Evaluating Activation and Deactivation of Vector Constructs Containing the Marker Gene, Luciferase ARPE-19 cells were seeded as described above. 12-24 hours later, cells were transfected with pAAV-LTetL-luc and pAAV-LCuL-luc. Media was replaced the next day and doxycycline or cumate was added to a subset of cells (FIG. 7). The media from the cells were assayed for the expression of marker gene, luciferase, using the Nano-Glo Luciferase assay on day 4 after having a media change on day 3. The Nano-Glow luciferase assay was performed as described above.

Following the luciferase assay, media was changed in all the wells. A subset of cells activated with doxycycline and cumate were washed to deactivate the vector. After 3 days of washes, Nano-Glow luciferase assay was again performed and results shown in FIG. 8.

Evaluating the Effects of Vector Constructs Containing Endo/Angiostatin on Angiogenesis The effects of the vector on angiogenesis were evaluated using a standard endothelial cell tube formation assay as per manufacturer's protocol (Life Technologies; Angiogenesis Starter Kit: A14609-01). Briefly, primary Human Umbilical Vein Endothelial Cells (HUVECs) were transfected with the cumate regulated vector containing endo/angiostatin (pAAV-LCuL-EAS) with or without Cre (as described above). The cells were washed within 24 hours of transfection, seeded on geltrex (basement membrane matrix) after 48 hours transfection. After 14-18 hours, the tubes were photographed and analysed with ImageJ Angiogenesis Analyser software (NIH; MD, USA). The schematic for the experiment is shown in FIG. 9 and the results are shown in FIG. 10.

Evaluating the Regulation of Inflammatory Markers in Vector Constructs Containing IL-10

ARPE-19 cells were seeded and transfected (as described above) with the vector containing Cu regulated IL-10, pAAV-LCuL-IL-10. This vector, containing the anti-inflammatory cytokine IL-10, was used to test the induction of proinflammatory signalling by measuring the expression of IL-6. Cre was used to activate the internal kill switch and silence the activated as well as the inactivated vector. After transfection of ARPE-19, the cells were washed for 2 days and the media collected on day 4 was used in enzyme linked immusorbent assay (ELISA) to determine the concentration of IL-6 and IL-10, as per manufacturer's directions (elisakit.com-0012, elisakit.com-0031). The schematic for the experiment is shown in FIG. 11 and the results are shown in FIG. 12.

Statistical Analysis

All statistical analysis was performed using Sigma Plot 13.0 (Systat Software; CA, USA). All differences in gene regulation of vectors were assessed by t-test with a p-value <0.05 considered statistically significant.

Example 2—Expression Vectors

Tetracycline or Cumate repressor genes (SEQ ID NOs: 2 and 3 respectively) were cloned into repressor cloning site 1 of the vector backbone (FIG. 1) using XbaI and EcoRI restriction sites. The corresponding promoter was cloned into the promoter cloning site 2 using BstBI and SalI restriction sites (SEQ ID NOs: 4 and 5 respectively). The conditionally regulated polypeptide was cloned into the GOI cloning site 3 using SalI and NheI restriction sites (GFP, IL-10, Endo/Angiostation fusion protein, IL-1RA or IL-10/IL-1RA genes; SEQ ID NOs: 7 to 11) or the compatible XhoI and XbaI sites (Nano-Luciferase; SEQ ID NO: 12). FIG. 2 shows a schematic of how the expression vectors were constructed.

Example 3—Kill Switch Activation

The expression vector was constructed with all expression sequences located within 2 LoxP sites (FIG. 1 and FIG. 2). In order to permanently silence expression, the cells were transfected with a vector expressing Cre. Cre removes all expression sequences by site-specific recombination at the two loxP sites (SEQ ID NO: 13). The resulting vector is absent of expression machinery and cannot induce transgene expression.

A human retinal pigmented epithelial cell line (aRPE-19) was transfected with vector constructs containing Tetracycline or Cumate regulatory elements or a CMV promoter, driving the expression of a marker gene, luciferase. Twenty-four hours later, the cells were treated with or without Tetracycline (Tet) or Cumate (Cu) and incubated for a further 48 hours before assessing the expression of luciferase. The ability of the system to kill expression of the transgene (luciferase) was examined by transfecting a Cre vector into the cells to cut out the expression sequences between LoxP sites. The cells were washed and regulator compounds (Tet and Cu) were added back daily until day 7 when media was assayed for changes in expression levels of luciferase.

Expression of luciferase in cells treated with the Tet vector with (pAAV-LTetL-luc ON) or without (pAAV-LTetL-luc OFF) Tet activation is shown in FIG. 5a. Expression of luciferase in cells treated with the Cu vector with or without Cu activation is shown in FIG. 5b. Expression of luciferase following transfection with CMV vectors, with or without Cre mediated excision is shown in FIG. 5c. Luciferase expression was effectively silenced in all Cre excised cells.

Example 4—Therapeutic Regulation

The Tet On system that was used is summarised in FIG. 6a. The EF1-HTLV promoter constitutively expresses a Tet transactivator protein that is unable to bind to Tet responsive elements (TRE) in the Tet promoter resulting in its inactivation and the lack of transgene expression. In the presence of Tet, the transactivator proteins bind to the Tet Response Elements (TRE) in the promoter, activating it and inducing expression of the transgene. The Cu On system that was used is summarised in FIG. 6b. In this system, the Cu repressor protein binds to the Cu operator sequence, in the absence of Cu, thus inactivating the promoter resulting in no transgene transcription. With the addition of Cu, the Cu binds to the repressor protein, bound to the Cu promoter, thus releasing the repressor allowing transgene transcription.

A human retinal pigmented epithelial cell line (aRPE-19) was transfected with vector constructs containing Tet or Cu regulatory sequences driving the expression of the marker gene luciferase. Twenty-four hours later, the cells were treated with or without Tet or Cu and incubated for a further 48 hours before assessing the expression of luciferase. The ability of the system to stop expression of the transgene (Luciferase) was examined by removing the Tet or Cu from the cells by washing prior to re-examining Luciferase expression. Cells without Tet or Cu were used as a control as were cells where Tet or Cu was not removed.

FIG. 8a shows the results from the luminescence assay performed on day 7 of the experiment using tetracycline as the agent to switch on transgene production. FIG. 8b shows the results from the luminescence assay performed on day 7 of the experiment using cumate as the agent to switch on transgene production. In both experiments, the substrate (Tet or Cu) was able to induce significant levels of luciferase expression and was regulated by the removal of the substrate resulting in significantly less luciferase being detected.

Example 5—Tube Formation Assay

Effects of a vector containing endo/angiostatin (EAS) flanked by LoxP sites on angiogenesis was assessed using a tube formation assay in primary human umbilical vein epithelial cells (HUVEC), with or without Cre (FIG. 9). Early passage (p2-4) HUVECs were transfected with the cumate regulated vector producing EAS (pAAV-LCuL-EAS). Two days post transfection, cells were counted and seeded in geltrex coated wells and incubated at 37° C., 5% $CO_2$ for 14-18 hours after which the tubes formed in the geltrex were photographed and analysed using ImageJ angiogenesis analyser.

FIG. 10A shows HUVEC tube formation in cells transfected with the non-EAS expressing pAAV-LCuL-EAS without Cu activation. FIG. 10B shows the inhibition of tube formation when HUVECs were treated with activated pAAV-LCuL-EAS. FIG. 10C shows the return of tube formation capacity when the activated pAAV-LCuL-EAS was excised by Cre. FIGS. 10D and 10E quantifies the total mesh area and total branch length respectively using ImageJ Angiogenesis Analyzer software. The pAAV-LCuL-EAS vector was able to reduce tube formation, which was largely reversed when the vector was excised by Cre.

Example 6—Pro-Inflammatory Signalling

Effects of a vector containing Cu regulated IL-10, flanked by LoxP sites on the induction of pro-inflamatory signalling was determined by measuring IL-6 expression with or without Cre (FIG. 11). A human retinal pigmented epithelial cell line (aRPE-19) was transfected with vector constructs containing Cu regulatory sequences driving the expression of anti-inflammatory IL-10. The negative control consisted of the IL-10 vector lacking Cu activation, treated with Cre. The IL-10 group consisted of the IL-10 vector activated by Cu. The killed group consisted of activated IL-10 vector, treated with Cre. Cells were assayed by ELISA for the expression of IL-10 and the pro-inflammatory marker IL-6.

FIG. 12 shows the results obtained from simultaneous ELISAs of IL-10 and IL-6 following transfection with cumate regulated vectors containing IL-10 with or without the addition of Cre. In cells treated with the negative control vector (without Cu and with Cre), the level of IL-10 detected was low, correlating to high levels of the proinflamatory IL-6. Conversely, cells treated with the Cu regulated IL-10 vector in the presence of Cu (IL-10 vector: on) expressed high levels of IL-10 which correlated to low levels of IL-6 expression. Vectors where the IL-10 was excised by Cre (IL-10 vector: killed) had IL-10 and IL-6 levels comparable to that of the negative control showing that expression of IL-10 was effectively silenced.

It will be appreciated by persons skilled in the art that numerous variations and/or modifications may be made to the disclosure as shown in the specific embodiments without departing from the spirit or scope of the disclosure as broadly described. The present embodiments are, therefore, to be considered in all respects as illustrative and not restrictive.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

The present application claims priority from AU 2018900206 filed 23 Jan. 2018, the entire contents of which are incorporated herein by reference.

The invention claimed is:

1. An expression vector comprising
a) a kill switch comprising a first site-specific recombination sequence and a second site-specific recombination sequence;
b) a regulatable element operably linked to a nucleic acid sequence encoding a therapeutic molecule, wherein activity of the regulatable element is regulated by a regulator compound; and
c) a constitutive promoter operably linked to a nucleic acid sequence encoding a regulator compound-binding polypeptide which is capable of binding a regulator compound, wherein upon binding the regulator compound, the regulator compound-binding polypeptide regulates expression of the therapeutic molecule,
wherein activation of the kill switch by recombination between the first site-specific recombination sequence and the second site-specific recombination sequence silences expression of the nucleic acid encoding the therapeutic molecule from the vector.

2. The expression vector of claim 1, wherein the first site-specific recombination sequence is positioned upstream of the nucleic acid sequence encoding the therapeutic molecule and the second site-specific recombination sequence is positioned downstream of the nucleic acid sequence encoding the therapeutic molecule, and/or wherein the first site-specific recombination sequence and the second site-specific recombination sequence are loxP sites.

3. The expression vector of claim 1, wherein upon binding of the regulator compound, the regulator compound-binding polypeptide
a) promotes expression of the therapeutic molecule, or
b) represses expression of the therapeutic molecule.

4. The expression vector of claim 1, wherein one or more or all of the following apply:
a) the regulator compound-binding polypeptide comprises one or more of a reverse tetracycline-controlled transactivator (rtTA), a tetracycline-controlled transactivator or a cysteine metabolism repressor (CymR);
b) the regulator compound is tetracycline, cumate, progesterone, a glucocorticoid, estrogen, or mifepristone;
c) the regulatable element comprises one or more of a tetracycline responsive element (TRE), a cumate operator (CuO), an ecdysone response element (EcRE), estrogen response element (ERE), a glucocorticoid response element (GRE), a progesterone response element (PRE), a heat shock sequence element (HSE), or a light inducible promoter;
d) the constitutive promoter is a composite human CMV-EF1-HTLV promoter;
e) the therapeutic molecule inhibits angiogenesis;
f) the therapeutic molecule:
comprises endostatin, angiostatin, or a fusion of endostatin and angiostatin;
is a binding protein;
comprises an antigen binding site of an antibody;
is selected from the group consisting of is ranibizumab, bevacizumab, and aflibercept;
inhibits inflammation; or
is interleukin 10 (IL-10), interleukin 1 receptor antagonist (IL-1RA); or a fusion of IL-10 and IL-1RA;
g) the vector further comprises a transcription blocker between the constitutive promoter and the regulatable promoter; and
h) the vector is a viral vector.

5. The expression vector of claim 1, wherein the vector is an adeno-associated virus (AAV) vector.

6. The expression vector of claim 1, wherein the therapeutic molecule is a nucleic acid or polypeptide.

7. A pharmaceutical composition comprising the expression vector of claim 1, and a pharmaceutically acceptable carrier, diluent or excipient.

8. A kit comprising the expression vector of claim 1 and an eye drop formulation comprising a regulator compound.

9. The kit of claim 8, further comprising a recombinase or an expression vector comprising a nucleic acid sequence encoding a recombinase and/or
an eye drop formulation comprising tetracycline, and
a Cre recombinase or an expression vector comprising a nucleic acid sequence encoding a Cre recombinase.

10. The expression vector of claim 1, wherein:
a) the kill switch comprising a first site-specific recombination sequence and a second site-specific recombination sequence comprises loxP sites;
b) the regulatable element comprises a tetracycline responsive element (TRE), a cumate operator (CuO), an ecdysone response element (EcRE), estrogen response element (ERE), a glucocorticoid response element (GRE), a progesterone response element (PRE), a heat shock sequence element (HSE), or a light inducible promoter;
c) the regulator compound-binding polypeptide comprises a reverse tetracycline-controlled transactivator (rtTA), a tetracycline-controlled transactivator or a cysteine metabolism repressor (CymR); and
c) the regulator compound is tetracycline, cumate, progesterone, a glucocorticoid, estrogen, or mifepristone.

* * * * *